(12) United States Patent
Ralph et al.

(10) Patent No.: US 10,227,287 B2
(45) Date of Patent: Mar. 12, 2019

(54) METHOD FOR DETECTING AND DETERMINING LEVELS OF MONOLIGNOL ESTER CONJUGATES INCORPORATED INTO LIGNIN AND COMPOUNDS RELATING THERETO

(71) Applicant: WISCONSIN ALUMNI RESEARCH FOUNDATION, Madison, WI (US)

(72) Inventors: John Ralph, Madison, WI (US);
Steven D Karlen, Verona, WI (US);
Fachuang Lu, Madison, WI (US);
Dharshana Padmakshan, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 194 days.

(21) Appl. No.: 14/985,720

(22) Filed: Dec. 31, 2015

(65) Prior Publication Data

US 2016/0187345 A1    Jun. 30, 2016

Related U.S. Application Data

(60) Provisional application No. 62/098,859, filed on Dec. 31, 2014.

(51) Int. Cl.
*C07C 69/73* (2006.01)
*C07C 69/007* (2006.01)
(Continued)

(52) U.S. Cl.
CPC ............ *C07C 69/73* (2013.01); *C07C 69/007* (2013.01); *C07C 69/16* (2013.01); *C07C 69/732* (2013.01);
(Continued)

(58) Field of Classification Search
CPC ...................................................... C07C 69/73
(Continued)

(56) References Cited

U.S. PATENT DOCUMENTS 8,569,465 B2    10/2013    Ralph et al.
2011/0003978 A1    1/2011    Ralph et al.
(Continued)

FOREIGN PATENT DOCUMENTS

WO    WO 2012/012698    1/2012
WO    WO 2013/052660    4/2013
WO    WO 2013/090814    6/2013

OTHER PUBLICATIONS

Fachuang Lu and John Ralph "Efficient Ether Cleavage in Lignins: The Derivatization Followed by Reductive Cleavage Procedure as a Basis for" Lignin and Lignan Biosynthesis Chapter 20, pp. 294-322 ACS Symposium Series, vol. 697, Aug. 13, 1998, American Chemical Society (Year: 1998).*

(Continued)

*Primary Examiner* — Christine T Mui
*Assistant Examiner* — Emily R. Berkeley
(74) *Attorney, Agent, or Firm* — Daniel A. Blasiole; DeWitt LLP

(57) ABSTRACT

Described is a method of detecting and/or determining levels of incorporation of monolignol ferulate conjugate esters into lignin by derivatizing the lignin, reductively cleaving the lignin, labeling the cleavage products, and then detecting cleavage products derived from monolignol ester conjugates via differential attachment of the label.

6 Claims, 10 Drawing Sheets
(9 of 10 Drawing Sheet(s) Filed in Color)

(51) Int. Cl.
| | |
|---|---|
| C07C 69/16 | (2006.01) |
| C07C 69/732 | (2006.01) |
| C07C 69/734 | (2006.01) |
| C07C 69/84 | (2006.01) |
| C07C 69/86 | (2006.01) |
| C07C 69/92 | (2006.01) |
| G01N 33/50 | (2006.01) |

(52) U.S. Cl.
CPC ............ *C07C 69/734* (2013.01); *C07C 69/84* (2013.01); *C07C 69/86* (2013.01); *C07C 69/92* (2013.01); *G01N 33/50* (2013.01); *C07B 2200/05* (2013.01); *G01N 2400/26* (2013.01); *G01N 2458/15* (2013.01); *G01N 2560/00* (2013.01)

(58) Field of Classification Search
USPC .......................................................... 422/63
See application file for complete search history.

(56) References Cited

U.S. PATENT DOCUMENTS

| | | |
|---|---|---|
| 2013/0203973 A1 | 8/2013 | Wilkerson et al. |
| 2013/0219547 A1 | 8/2013 | Wilkerson et al. |
| 2015/0020234 A1 | 1/2015 | Wilkerson et al. |

OTHER PUBLICATIONS

Clemens Schwarzinger, Manuela List "Identification of marker compounds in pyrolysis—GC/MS of various acetylated wood types" J. Anal. Appl. Pyrolysis 87 (2010) 144-153 (Year: 2010).*
Bartley et al., Overexpression of a BAHD acyltransferase, OsAt10, alters rice cell wall hydroxycinnamic acid content and saccharification. Plant Physiol 161, 1615 (2013).
Boerjan et al., Lignin biosynthesis. Annu. Rev. Plant Biol. 54, 519 (2003).
Bonawitz et al., Disruption of the transcriptional coregulatory complex Mediator rescues the stunted growth of a lignin-deficient *Arabidopsis* mutant. Nature, in press (2014).
Chang et al., Comparative studies on cellulolytic enzyme lignin and milled wood lignin of sweetgum and spruce. Holzforschung 29, 153 (1975).
Chen et al., Lignin modification improves fermentable sugar yields for biofuel production. Nature Biotechnol. 25, 759 (2007).
Chen et al, A polymer of caffeyl alcohol in plant seeds. Proc. Natl. Acad. Sci. 109, 1772 (2012).
Coleman et al., RNAi-mediated suppression of p-coumaroyl-CoA 3'-hydroxylase in hybrid poplar impacts lignin deposition and soluble secondary metabolism. Proc. Natl. Acad. Sci. 105, 4501 (2008).
Durrett et al., A distinct DGAT with sn-3 acetyltransferase activity that synthesizes unusual, reduced-viscosity oils in Euonymus and transgenic seeds. Proc. Natl. Acad. Sci. 107, 9464 (2010).
Edgar et al., MUSCLE: multiple sequence alignment with high accuracy and high throughput. Nucleic Acids Res 32, 1792 (2004).
Grabber et al., Coniferyl ferulate incorporation into lignin enhances the alkaline delignification and enzymatic degradation of maize cell walls. Biomacromolecules 9, 2510 (2008).
Huson et al., Dendroscope: An interactive viewer for large phylogenetic trees. Bmc Bioinformatics 8, 460 (2007).
Karimi et al., Modular cloning in plant cells. Trends Plant Sci. 10, 103 (2005).
Kolosova et al., Isolation of high-quality RNA from gymnosperm and angiosperm trees. Biotechniques 36, 821 (2004).

Li et al., The Class II KNOX gene KNAT7 negatively regulates secondary wall formation in *Arabidopsis* and is functionally conserved in Populus. New Phytologist 194, 102 (2012).
Li, et al., Improvement of biomass through lignin modification. Plant J. 54, 569 (2008).
Lu et al., Detection and determination of p-coumaroylated units in lignins. J. Agr. Food Chem. 47, 1988 (1999).
Martone et al., Discovery of lignin in seaweed reveals convergent evolution of cell-wall architecture. Current Biology 19, 169 (2009).
Petrik et al., p-Coumaroyl-CoA:Monolignol Transferase (PMT) acts specifically in the lignin biosynthetic pathway in Brachypodium distachyon. Plant J., in press (accepted Dec. 17, 2013) (2014).
Ralph et al., Lignins: natural polymers from oxidative coupling of 4-hydroxyphenylpropanoids. Phytochem. Revs. 3, 29 (2004).
Ralph et al., Lignification: Are lignins biosynthesized via simple combinatorial chemistry or via proteinaceous control and template replication? in Recent Advances in Polyphenol Research, vol. 1, F. Daayf, A. El Hadrami, L. Adam, G. M. Ballance, Eds. (Wiley-Blackwell Publishing, Oxford, UK, 2008), vol. 1, pp. 36-66.
Ralph, Hydroxycinnamates in Lignification. Phytochem. Revs. 9, 65 (2010).
Robinson et al., Rapid analysis of poplar lignin monomer composition by a streamlined thioacidolysis procedure and near-infrared reflectance-based prediction modeling. Plant J. 58, 706 (2009).
Santoro et al., A high-throughput platform for screening milligram quantities of plant biomass for lignocellulose digestibility. Bioenergy Research 3, 93 (2010).
Schmidt et al., TREE-PUZZLE: maximum likelihood phylogenetic analysis using quartets and parallel computing. Bioinformatics 18, 502 (2002).
Stewart et al., The effects on lignin structure of overexpression of ferulate 5-hydroxylase in hybrid Poplar. Plant Physiol. 150, 621 (2009).
Subramanian et al., a suite of tools and application notes for in vivo protein interaction assays using bioluminescence resonance energy transfer (BRET). Plant J. 48, 138 (2006).
Vanholme et al., Lignin engineering. Curr. Opin. Plant Biol. 11, 278 (2008).
Vanholme et al., Engineering traditional monolignols out of lignins by concomitant up-regulation F5H1 and down-regulation of COMT in *Arabidopis* Plant J. 64, 885 (2010).
Vanholme et al., Metabolic engineering of novel lignin in biomass crops. New Phytologist 196, 978 (2012).
Vanholme et al., Caffeoyl shikimate esterase (CSE), a newly discovered gene in the lignin biosynthetic pathway. Science 341, 1103 (2013).
Wagner et al., Exploring lignification in conifers by silencing hydroxycinnamoyl-CoA:shikimate hydroxycinnamoyltransferase in Pinus radiata. Proc. Natl. Acad. Sci. 104, 11856 (2007).
Weng et al., Over-expression of F5H in COMT-deficient *Arabidopsis* leads to enrichment of an unusual lignin and disruption of pollen wall formation. Plant J. 64, 898 (2010).
Wilkerson et al., Monolignol ferulate transferase introduces chemically labile linkages into the lignin backbone. Science, 2014, 344, 90-93.
Withers et al., Identification of a grass-specific enzyme that acylates monolignols with p-coumarate. J. Biol. Chem. 287, 8347 (2012).
Xie et al., Optimization and comparison of five methods for extraction of coniferyl ferulate from Angelica sinensis. Molecules 14, 555 (2009).
Zhao et al., Loss of function of Cinnamyl Alcohol Dehydrogenase 1 causes accumulation of an unconventional lignin and a temperature-sensitive growth defect in Medicago truncatula. Proc. Natl. Acad. Sci. 110, 13660 (2013).
Zhu et al., Preparation of monolignol γ-acetate, γ-p-hydroxycinnamate, and γ-p-hydroxybenzoate conjugates: Selective deacylation of phenolic acetates with hydrazine acetate. RSC Advances 3, 21964 (2013).

* cited by examiner

METHOD FOR DETECTING AND DETERMINING LEVELS OF MONOLIGNOL ESTER CONJUGATES INCORPORATED INTO LIGNIN AND COMPOUNDS RELATING THERETO

FEDERAL FUNDING STATEMENT

This invention was made with government support under DE-FC02-07ER64494 awarded by the US Department of Energy. The government has certain rights in the invention.

BACKGROUND

Lignin is a complex phenolic polymer that fortifies plant cell walls and is essential for plant growth and development. The presence of lignin in biomass, however, acts as a major impediment to industrial processing. Research efforts have therefore focused on altering the natural lignification processes to produce plants with cell walls that process more readily to liberate carbohydrates with minimal input (Li et al. 2008, Chen et al. 2007, Vanholme et al. 2008, Ralph et al. 2004, Boerjan et al. 2003).

The biosynthetic steps to produce the monomers employed in the synthesis of lignin have been elucidated (Li et al. 2008, Ralph et al. 2004, Boerjan et al. 2003). New genes relevant to lignin production continue to be discovered (Vanholme et al. 2008, Withers et al. 2012), and several transcription factors integral to controlling the lignin biosynthetic network have been identified (Li et al. 2012). Perturbations of these and other processes can lead to the synthesis of lignins that incorporate alternative monomers. These monomers are usually derived from products of incomplete monolignol biosynthesis. These discoveries spawned the idea that lignins could be designed to encompass significant structural alterations that would engender unique properties (Ralph et al. 2004, Vanholme et al. 2012, Ralph 2010).

Studies of natural plant tissues, along with those from mutants and transgenics with misregulated monolignol biosynthetic genes, have led to some remarkable discoveries, including plants that produce homopolymers from a range of "traditional" monomers (e.g., p-coumaryl and sinapyl alcohols (Stewart et al. 2009, Bonawitz et al. 2014)) as well as "non-traditional" monomers (e.g., caffeyl and 5-hydroxyconiferyl alcohols, and the hydroxycinnamaldehydes (Chen et al. 2012, Vanholme et al. 2010, Weng et al. 2010, Zhao et al. 2013). These observations clearly illustrate the pliability of the lignification process (Ralph et al. 2004, Ralph 2010, Ralph et al. 2008). The formal "design" of an improved polymer using unconventional monomers therefore seems to be a feasible path to tailor plants with superior processing properties for both paper and biofuels production (Vanholme et al. 2012, Ralph 2010, Wilkerson et al. 2014, Grabber et al. 2008).

Redesigning lignin to be more amenable to chemical depolymerization can lower the energy required for industrial processing. In this vein, lignin has been engineered to contain readily cleavable ester bonds in the form of monolignol ester conjugates in the polymer backbone, improving its degradability. See U.S. Pat. No. 8,569,465, US 2011/0003978, US 2013/0203973, US 2013/0219547, US 2015/0020234, WO 2012/012698, WO 2013/052660, and WO 2013/090814. Poplar trees, for example, have been engineered to introduce ester linkages into the lignin polymer backbone by augmenting the monomer pool with monolignol ferulate conjugates (Wilkerson et al. 2014). Enzyme kinetics, in planta expression, lignin structural analysis, and improved cell wall digestibility after mild alkaline pretreatment demonstrated that these trees produce the monolignol ferulate conjugates, export them to the cell wall, and utilize them during lignification.

Tailoring plants to employ monolignol ester conjugates during cell wall biosynthesis is a promising way to produce plants that are designed for deconstruction. Methods for directly detecting and determining levels of such monolignol ester conjugates incorporated into plant lignin, however, are not known in the art and are therefore needed.

SUMMARY OF THE INVENTION

Disclosed herein are methods for detecting and determining levels of monolignol ester conjugates incorporated into plant lignin and compounds relating thereto.

One aspect of the invention includes a method of detecting and, optionally, determining a level of incorporation of monolignol ester conjugates into lignin. The method comprises derivatizing lignin to acylate at least a portion free phenolic and aliphatic hydroxyls and to halogenate at least a portion of benzylic alcohols present in the lignin, to yield derivatized lignin; treating the derivatized lignin with a reducing agent to cleave at least a portion of the derivatized lignin, to yield lignin cleavage products; acetylating at least a portion of free hydroxyl groups in the lignin cleavage products with a labeled acetylation agent, to yield labeled lignin fragments; and detecting the labeled lignin fragments.

The method may optionally comprise determining the level of incorporation of monolignol ester conjugates in the lignin by measuring an amount or a concentration of labeled lignin fragments. Liquid or gas chromatography and mass spectrometry, among other methods, may be used to measure the amount or concentration of labeled lignin fragments.

The lignin may be derivatized with an acetyl halide, such as acetyl bromide. The step of derivatizing the lignin may comprise derivatizing extracted cell wall material or isolated lignin from plants, plant parts, or plant cells.

The labeled acetylation agent may comprise labeled acetic anhydride. The labeled acetic anhydride may be labeled with an isotope. The labeled acetic anhydride may comprise deuterium-labeled acetic anhydride.

The labeled lignin fragments produced in the acetylation step may comprise labeled monolignol ester conjugates comprising a monolignol moiety and a carboxylate moiety. The monolignol moiety and the carboxylate moiety may both be independently acetylated with the labeled acetylation agent. The carboxylate moiety may be selected from the group consisting of p-hydroxybenzoate, p-coumarate, ferulate, and sinapate.

Another aspect of the invention includes compounds generated and detected by the methods described herein as well as compounds for use as standards for the methods described herein. Such compounds include the compounds of Formula I:

Formula I

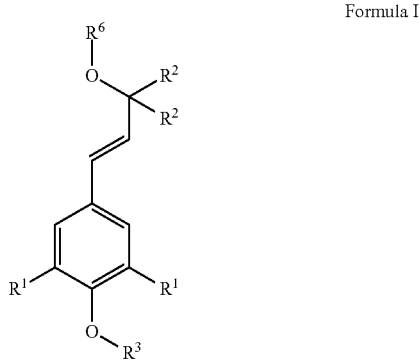

wherein:

R[1] is independently selected from the group consisting of hydrogen and —OCH$_3$;

R[2] is independently selected from the group consisting of $^1$H, $^2$H, and $^3$H;

R[3] is:

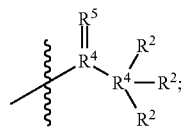

R[4] is independently selected from the group consisting of $^{12}$C, $^{13}$C, and $^{14}$C;

R[5] is independently selected from the group consisting of $^{16}$O, $^{17}$O, and $^{18}$O;

R[6] is R[3] or R[7];

R[7] is:

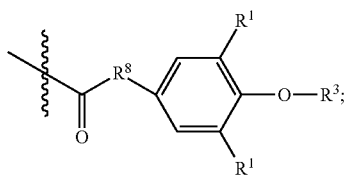

and

—R[8]— is —(CR[2]$_2$)$_{1-6}$— or a single bond, wherein all of the R[2], R[4], and R[5] present in the compound are not simultaneously $^1$H, $^{12}$C, and $^{16}$O, respectively.

In some compounds, each R[2] in each R[3] may be independently selected from the group consisting of $^2$H and $^3$H. R[6] in some of these compounds may be R[7]. At least one R[1] in R[7] in some of these compounds may be —OCH$_3$.

In some compounds, R[6] is R[7]. At least one R[1] in R[7] in some of these compounds may be —OCH$_3$.

Another aspect of the invention comprises compositions comprising one or more compounds of Formula I. In some versions, the composition comprises fewer than about 3 different species of Formula I. In some versions, the composition comprises about one and only one species of Formula I.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A: Mass spectra for compounds 8G and 8s from Q3 scans on a GC-triple-quad mass spectrometer. Molecular ions (m/z 442, 472) lose ketene (m/z 42) to yield the base peak (m/z 400, 430). FIG. 3B: Triple-quad multiple reaction monitoring (MRM) chromatograms of the Poplar-derived m/z 400 parent ion to the diagnostic 195, 163, and 131 product ions and m/z 430 parent ion to the 193, 161, and 133 product ions. The numbers for the cis- and trans-isomers are the MRM intensities for transgenic CesA8::FMT-6 in black and wild-type in red (with the corresponding measured intensities from the synthetic standards in parentheses) relative to the 400→131 (CA-FA) and 430→161 (SA-FA) peak for each. All of the data for the Poplar-released conjugates match (by retention times, mass spectra, collision-induced fragmentation, and MRM relative intensities of daughter ions).

FIGS. 4C and 4D show the measured ion ratio as determined by GC-MRM-MS and GC-SIM-MS for compounds 8G$_a$ (FIG. 4C) 8G$_b$ (FIG. 4C), 8G$_e$ (FIG. 4D), and 8G$_d$ (FIG. 4D) from analysis of transgenic Poplar CesA8::FMT-5 (Wilkerson et al. 2014) using labeled reagents, and the mass spectral fragmentation ions from labeled compounds 8G$_a$ (FIG. 4C) 8G$_b$ (FIG. 4C), 8G$_e$ (FIG. 4D), and 8G$_d$ (FIG. 4D). FIG. 4E shows a GC-MRM-MS chromatogram of the product ions from analysis of the transgenic Poplar CesA8::FMT-5, using labeled reagents, which indicates that coniferyl ferulate is indeed incorporated into the backbone of lignin polymer of this FMT-Poplar.

DETAILED DESCRIPTION

Figure 1A:
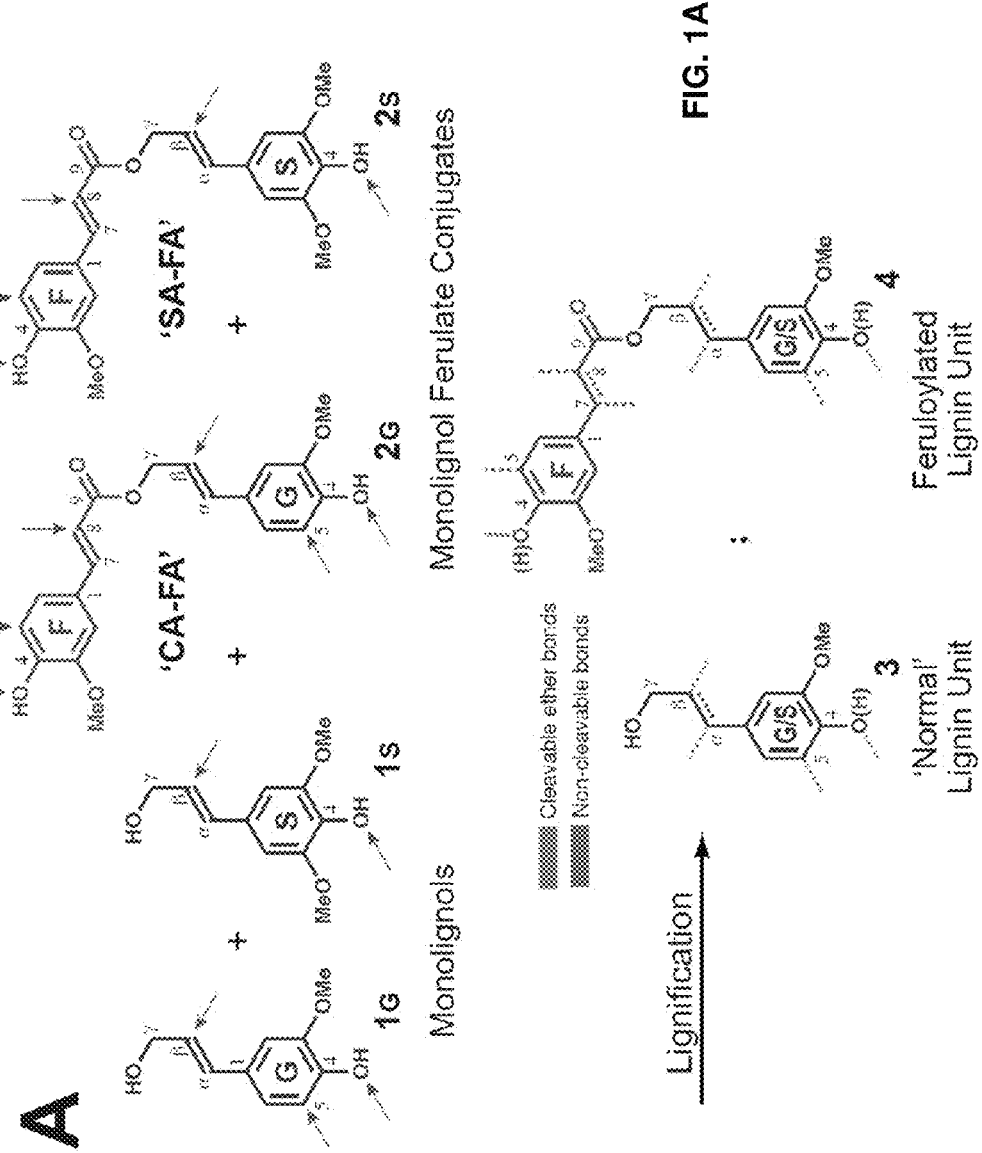
FIGS. 1A and 1B are schema showing lignification with exemplary monolignol ester conjugates coniferyl ferulate and sinapyl ferulate (FIG. 1A) and the detection of these incorporated monolignol ester conjugates according to an exemplary method of the invention (FIG. 1B). Sites of radical coupling for the monolignols 1G/1s and the conjugates 2G/2s are indicated by magenta arrows. In the final lignin units 3 and 4, cleavable ether bonds are indicated by dotted bonds in cyan, non-cleavable bonds in brown.

The invention provides methods of detecting incorporation of monolignol ester conjugates into lignin. Monolignol ester conjugates are esters comprising a monolignol moiety esterified to a carboxylate moiety. The monolignol may include any monolignol capable of incorporating into lignin. Exemplary monolignols include p-coumaryl alcohol, coniferyl alcohol, and sinapyl alcohol. Coniferyl alcohol and sinapyl alcohol are shown as 1G and 1s, respectively, in FIG. 1A. p-Coumaryl alcohol differs from coniferyl alcohol and sinapyl alcohol by lacking the phenolic methoxy groups. The carboxylate moiety may include any compound comprising a carboxylate group. The carboxylate moiety is preferably a phenolic carboxylate. Exemplary phenolic carboxylates include p-hydroxybenzoate, p-coumarate, ferulate, and sinapate. Acetylated derivatives of monolignol ester conjugates comprising these phenolic carboxylates are shown in the second, third, fourth, and fifth columns, respectively, of FIG. 2. A ferulate moiety is also shown as the red portion of coniferyl ferulate 2G and sinapyl ferulate 2s in FIG. 1A. Beyond coniferyl ferulate and sinapyl ferulate as shown in FIG. 1A, other exemplary monolignol ester conjugates that can be detected and quantitated in the present methods include p-coumaryl ferulate, coniferyl p-hydroxybenzoate, sinapyl p-hydroxybenzoate, p-coumaryl p-hydroxybenzoate, coniferyl coumarate, sinapyl coumarate, p-coumaryl coumarate, coniferyl sinapate, sinapyl sinapate, and p-coumaryl sinapate, Unequivocally determining that plants are capable of incorporating monolignol ester conjugates into the lignin polymer is particularly challenging because compounds such as ferulate, coumarate, and others naturally integrally incorporate into lignins by highly complex combinatorial radical coupling. However, the methods described herein are capable of cleaving the lignin-signature β-ether bonds selectively—leaving γ-esters intact. The methods described herein make it possible to show that novel monolignol ester conjugates are indeed incorporated into lignin.

Only a small fraction of the expected structures in the lignin polymers that would result from incorporating monolignol ferulate conjugates into lignins can be cleaved using the methods described herein. See FIG. 1A, for example. This releases monolignol ester conjugates that are quantifiable by a variety of purification and analytic methods such as GC-MS, LC-MS, and others. Importantly, a double bond between the α and β carbons in the monolignol moiety of the released monolignol ester conjugates (see, for example, 8 in FIG. 1B), arises only from reductively cleaving the β-ether bond. The release of monolignol ester conjugates with this double bond therefore indicates that the monolignol ester conjugate has incorporated into the polymer by radical coupling.

An important feature of the present invention is that the depolymerization of the lignin under mild conditions allows for detection of monolignol ester conjugate incorporation into the lignin backbone via both of the monolignol unit and the carboxylate unit. The independent incorporation of both units into the lignin backbone, rather than incorporation of only the monolignol unit, rendering the carboxylate unit merely as a pendent group, is critical for generating lignin more amenable to depolymerization through cleavage of the ester. See, e.g., U.S. Pat. No. 8,569,465.

Another important feature of the present invention is the ability to quantify the level of monolignol ester conjugate incorporation. Quantifying the level of incorporation of monlignol ester conjugates is a challenge. Currently, no method exists for the quantification of the arabinoxylan-bound ferulates that are incorporated into grass lignins. It has remained extremely difficult even to detect them, e.g., by NMR, decades after their discovery. This is due in part to the huge range of combinatorial products encountered.

Figure 1B:
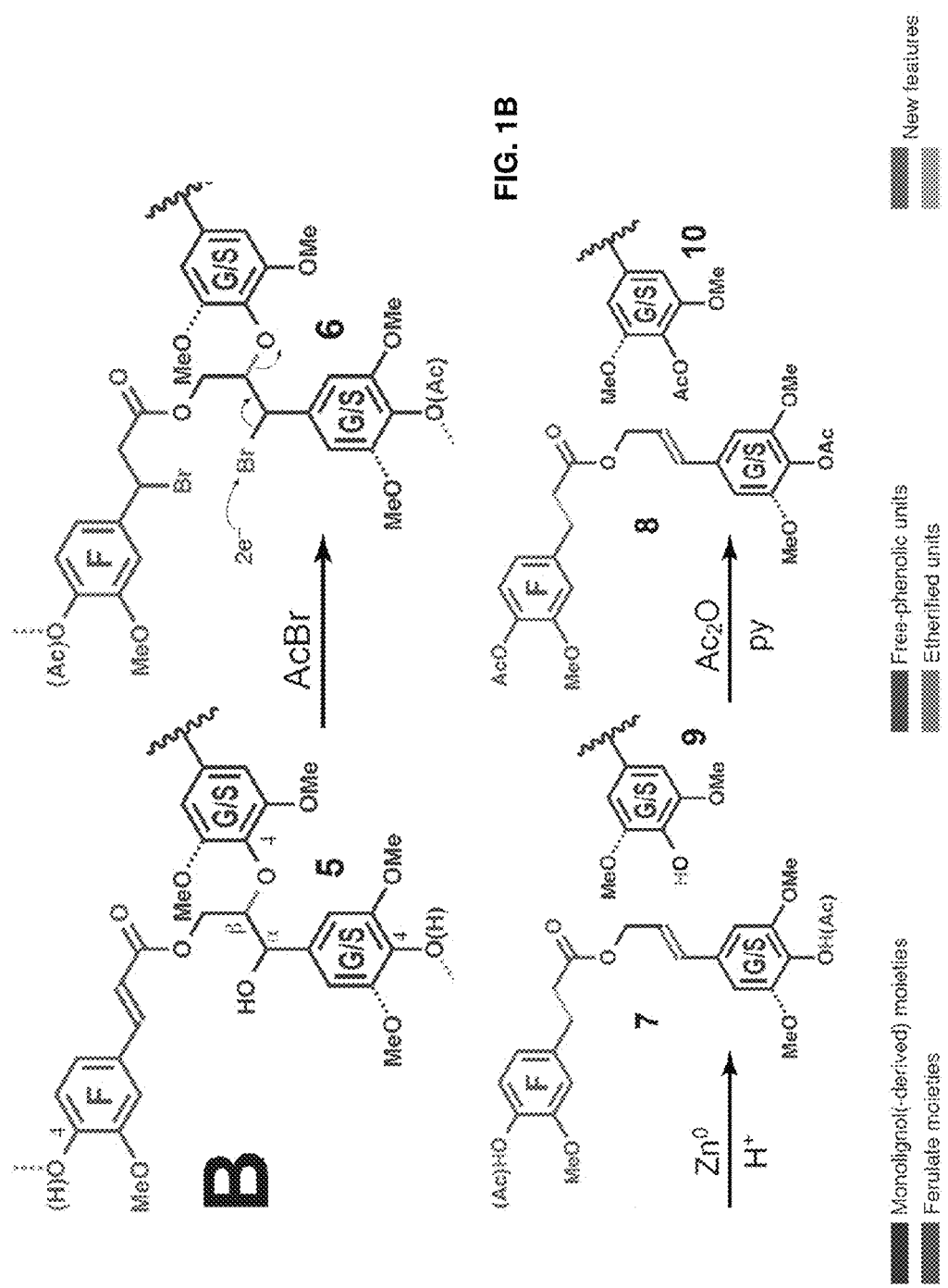

Lignification with exemplary monolignol ester conjugates coniferyl ferulate and sinapyl ferulate and the detection of these incorporated monolignol ester conjugates according to an exemplary method of the invention are shown in FIGS. 1A and 1B. As shown in FIG. 1A, lignification of monolignols coniferyl alcohol 1G and sinapyl alcohol 1s by combinatorial radical cross-coupling reactions produces a lignin in which the units can be represented by generic structure 3. Analogous lignification of monolignol ferulate conjugates coniferyl ferulate 2G and sinapyl ferulate 2s produces structural units 4 in which lignin moieties are γ-acylated by ferulate.

In FIG. 1B, structure 5 represents one of the many possible structures encompassed by structure 4. Structure 5 is derivatized with an acetyl halide such as acetyl bromide to acylate free phenolic groups and halogenate benzylic alcohols present in the lignin, thereby yielding a structure such as structure 6. Structure 6 is then reduced with a reducing agent such as zinc nanopowder to yield structures such as structures 7 and 9. The reduction de-halogenates the lignin, generates the signature double bond between the α and β carbons on the monolignol moiety, and breaks the ether bonds to yield free hydroxyls while leaving the ester bonds intact. The free hydroxyls are then acetylated with a labeled acetylation agent such as perdeuteroacetic anhydride to yield a structure such as structures 8 and 10. Because the initial acetylation step "masks" the free hydroxyls in the original lignin, the second acetylation step acetylates only the hydroxyls derived from phenolic ether linkages present in the initial structure 5 and effectively labels these phenolic ether linkages. Accordingly, products 8 with only one labeled acetyl group are indicative of only one of the two ester moieties having been incorporated into the lignin. Products 8 with two labeled acetyl groups are indicative of both of the two ester moieties having been independently incorporated into the initial lignin. These products are detectable and quantifiable using a variety of methods as described elsewhere herein.

The present method releases conjugates 8 that diagnostically result from structures 5 within the lignin. The crucial double bond (colored green in 8) arises only upon cleavage of the signature lignin β-ether bonds. The ferulate moiety remains attached to its parent unit. The method thus releases an acetylated dihydro analog (8 in FIG. 1A) of the monolignol ester conjugate that was originally incorporated into the lignin. This occurs via reactions that specifically cleave lignin β-ethers but leave lignin γ-esters intact. Because the initially free-phenolic units (versus etherified units) are acetate-tagged differentially at the stage of intermediate 7, acetylation with the labeled acetylation reagent in the final step reveals the etherification profile of the released units as they appeared in the cell wall. While structures 5 shown in FIG. 1B are only a small fraction of the many structures (represented by the generic structure 4) that can result when the combinatorial radical coupling reactions incorporate monolignol ferulates into lignin, they are the only components that can generate the diagnostic product 8.

The process shown in FIGS. 1A and 1B for detecting incorporation of coniferyl ferulate and sinapyl ferulate in lignin can be used to detect incorporation of any monolignol ester conjugate in lignin. Examples include p-coumaryl ferulate, coniferyl p-hydroxybenzoate, sinapyl p-hydroxybenzoate, p-coumaryl p-hydroxybenzoate, coniferyl coumarate, sinapyl coumarate, p-coumaryl coumarate, coniferyl sinapate, sinapyl sinapate, p-coumaryl sinapate, among others.

The derivatization of lignin may be performed with any acetyl halide, including acetyl bromide, acetyl fluoride, acetyl chloride, and acetyl iodide.

The reduction of the initially acetylated lignin may be performed with any reducing agent. Exemplary reducing agents, in addition to zinc nanopowder, include metals, such as Li, Na, Mg, Al, Cr, Fe, $Sn^{2+}$, $Cu^+$, Ag, $2Br^-$, $2Cl^-$, $Mn^{2+}+4H_2O$, $2F^-$, K, Ca, and Ba; compounds that contain the $H^-$ ion, such as NaH, LiH, $LiAlH_4$ and $CaH_2$; and others, including $H_2(g)+2OH^-$, $H_2$, lithium aluminum hydride (LiAlH$_4$), sodium amalgam, diborane, sodium borohydride (NaBH$_4$), compounds containing the $Sn^{2+}$ ion such as tin(II) chloride and others, sulfite compounds, hydrazine, zinc-mercury amalgam, diisobutylaluminum hydride (DIBAL-H), lindlar catalyst, oxalic acid ($C_2H_2O_4$), formic acid (HCOOH), ascorbic acid ($C_6H_8O_6$), phosphites, hypophosphites, phosphorous acid, dithiothreitol (DTT), compounds containing the $Fe^{2+}$ ion such as iron(II) sulfate, carbon monoxide (CO), carbon (C), tris(2-carboxyethyl)phosphine HCl (TCEP), and others.

Perdeuteroacetic anhydride is an exemplary labeled acetylation agent. However, any isotope-labeled acetic anhydride may be used. "Isotope" used in this context refers to a non-predominant isotope of an atom, e.g., an isotope having a relative abundance of less than about 95%, 90%, 80%, 70%, 60%, 50%, 40%, 30%, 20%, 10%, 5%, or 1% in nature. Exemplary isotopes for H, C, and O, include $^2H$, $^3H$, $^{13}C$, $^{14}C$, $^{17}O$, $^{18}O$. The isotope-labeled acetic anhydride may include any one or more of these isotopes.

The terms "label," "labelled," etc. are defined broadly herein to include molecular markers, labels, or probes of any structure or configuration that can be detected by any means, both now known or developed in the future. The terms "marker," "label," and "probe," are used synonymously and include, without limitation, radioactive labels (specifically including isotopes of hydrogen, carbon, and oxygen), fluorescent labels, chromophoric labels, affinity-based labels (such as antibody-type markers), and the like. Conventional radioactive and stable isotopes used for detection include, without limitation, $^2H$, $^3H$, $^{13}C$, $^{14}C$, $^{17}O$, $^{18}O$, and many others. In the case of stable isotopes, detection of labelled species can be achieved via mass spectrometry (due to the different m/z values of the isotopes). A host of isotopically enriched reagents are available from several commercial suppliers, most notably Sigma-Aldrich. A large number of fluorescent and chromophoric probes are known in the art and are commercially available from numerous worldwide suppliers, including Life Technologies (Carlsbad, Calif., USA), Enzo Life Sciences (Farmingdale, N.Y., USA), and Sigma-Aldrich (St. Louis, Mo., USA).

Exemplary detectable compounds generated by the methods of the invention are provided by Formula I:

Formula I

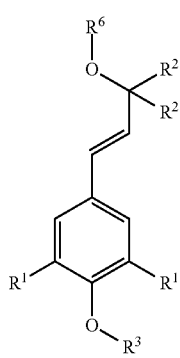

wherein:
$R^1$ is independently selected from the group consisting of hydrogen and —OCH$_3$;
$R^2$ is independently selected from the group consisting of $^1H$, $^2H$, and $^3H$;
$R^3$ is:

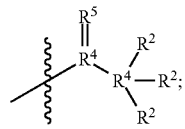

$R^4$ is independently selected from the group consisting of $^{12}C$, $^{13}C$, and $^{14}C$;
$R^5$ is independently selected from the group consisting of $^{16}O$, $^{17}O$, and $^{18}O$;
$R^7$ is:

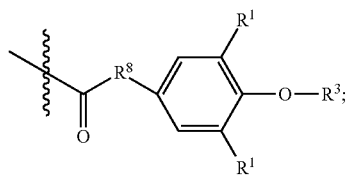

and
—$R^8$— is —(CR$^2_2$)$_{1-6}$— or a single bond.

Figure 2:
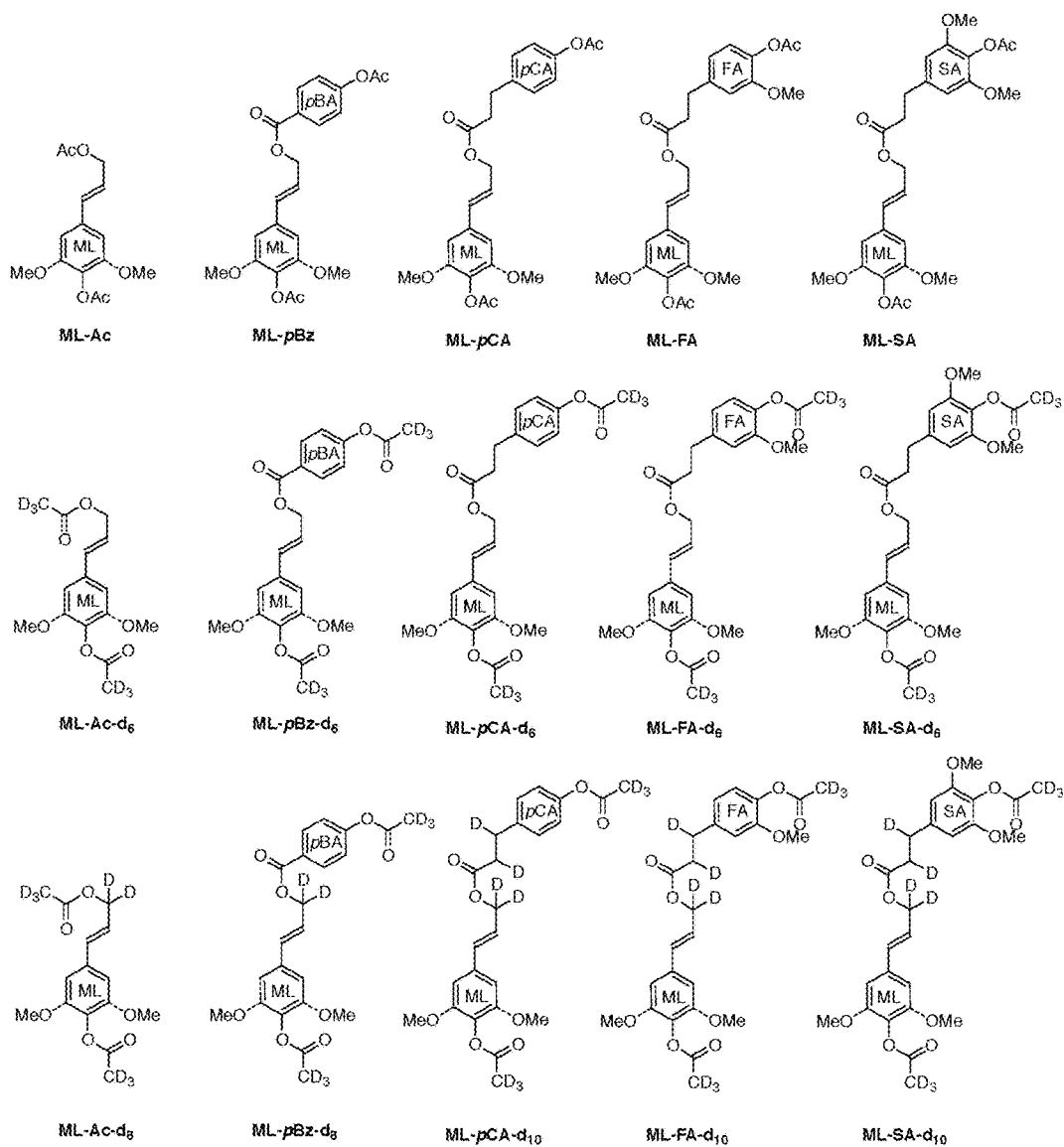
FIG. 2 shows exemplary compounds of the invention.

Accordingly, standards for use in detecting and quantitating the compounds generated by the methods of the invention are also provided by Formula I. Exemplary compounds of Formula I are shown in FIG. 2. The compounds shown in FIG. 2 are acetylated versions of monolignol ester conjugates comprising sinapyl alcohol (containing a syringyl unit) as the monolignol moiety. Other exemplary compounds include the compounds shown in FIG. 2 but with p-coumaryl alcohol (containing a p-hydroxyphenyl unit) or coniferyl alcohol (containing a guaiacyl unit) as the monolignol moiety. The detection and quantitation of the compounds of Formula I provides information on the type and level of incorporation of monolignol ester conjugates in lignin.

Detection of compounds of Formula I comprising one or more labeled acetyl groups is critical for determining the type and extent of incorporation of monolignol ester conjugates. Accordingly, compositions comprising a compound of Formula I wherein all of the $R^2$, $R^4$, and $R^5$ present in the compound are not simultaneously $^1H$, $^{12}C$, and $^{16}O$, respectively, are provided as an aspect of the invention. One to three of the $R^2$ in each $R^3$ of Formula I may be $^2H$ and/or $^3H$. If more than one $R^2$ in $R^3$ are not $^1H$, such $R^2$ are preferably all $^2H$ or all $^3H$. However, mixtures of $^2H$ and $^3H$ are also acceptable. Alternatively or additionally, one or both of the $R^4$ in each $R^3$ of Formula I may be $^{13}C$ and/or $^{14}C$. If both of the $R^4$ in $R^3$ are not $^{12}C$, both $R^4$ are preferably both $^{13}C$ or $^{14}C$. However, mixtures of $^{13}C$ and $^{14}C$ are also acceptable. Alternatively or additionally, the $R^5$ in each $R^3$ may be $^{17}O$ or $^{18}O$.

The compositions of the invention preferably comprise substantially purified compounds of Formula I. Accordingly, the composition preferably comprises fewer than about 20, about 15, about 10, about 5, or about 3 species of Formula I or comprises about one and only one species of Formula I. "Species" used in this context refers to a set of identical compounds of Formula I in which each corresponding R"

among the compounds is exemplified by the same substituent. The set of identical compounds may be any non-empty set comprising one or more copies of identical compounds. For the purposes of the present disclosure, stereoisomers do not constitute different species. The species may be purified by any available method, including liquid chromatography, gas chromatography, affinity chromatography, or other physical or chemical purification methods.

The methods described herein may also be used for detecting and quantitating incorporation of other non-standard lignin monomers, including non-ester monomers.

The ability to unambiguously determine that plants biosynthesize non-standard lignin monomers, transport these lignin monomers intact to the lignifying zone, and integrate the lignin monomers into the plant lignin is key to the development and deployment of modified lignin technology. Such an ability is provided by the methods, compounds, and compositions of the present invention.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more," unless explicitly stated to be otherwise. The word "or" is used inclusively, as in "and/or."

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

EXAMPLES

The following examples are included to provide a more complete disclosure of the methods described and claimed herein. The examples do not limit the scope of the claims in any fashion.

Sample Preparation

Analysis of lignin in biomass according to the present invention is preferably performed on solvent-soluble extractive-free ground samples with a consistent particle size that can pass a 1 mm mesh, or on isolated lignins. (This methodology can be applied to larger particle size samples at a cost of reaction yield and reproducibility.) Using biomass that has not been extracted is possible. However, there is then no way to determine if the diagnostic products are from cell-wall-bound monomers or from free monomer-containing extractives. There are many common techniques for the preparation of extract-free cell walls. One such method is to coarsely grind material using a Wiley mill with, e.g., a 1 mm screen, and then to solvent extract the ground material with water (1 g, 3×40 mL), then with 80% ethanol (3×40 mL), and finally with acetone (3×40 mL). The sample is then dried under vacuum.

The use of isolated lignins provides the best quality results because of the reduced polysaccharide background reactions and products that can interfere with the separation (gas chromatography (GC) or liquid chromatography (LC)) and analytical methods (mass spectrometry (MS)). Lignin fractions can be obtained through a wide variety of techniques. One method is to use pretreatment with crude cellulases to remove most of the polysaccharides and retain the lignin. Thus, an enzyme lignin (EL) can be prepared from ball-milled material as described previously (Chang et al. 1975, Wagner et al. 2007). Briefly, ball-milled extract-free biomass (1 g) in a 50 mL centrifuge tube with 40 mL sodium acetate buffer (pH 5.0) and 40 mg crude cellulase (Cellulysin®, EMD biosciences, CA) is incubated in a shaker at 35° C. for 3 days. The residue is recovered after centrifugation and washed with the buffer (40 mL). The washed residue is then treated with the crude cellulase (40 mg) again for 3 days. The residue is washed with water (3×40 mL) and recovered by centrifugation. The EL (10-30% of the ball-milled biomass) is obtained after freeze-drying under high vacuum.

Synthesis of Authentic Coniferyl and Sinapyl Dihydroferulate Standards

Coniferyl dihydroferulate $8_G$ and sinapyl dihydroferulate $8_S$ (FIG. 1B) are synthesized from coniferaldehyde or sinapaldehyde and dihydroferulic acid (4-hydroxy-3-methoxyphenylpropionic acid) according to the method described previously for the p-coumarate analog (Lu et al. 1999), or via a convenient new method (Zhu et al. 2013). The various deutero-labeled standards are synthesized using isotopically labeled reagents following the same protocols.

Derivatization Followed by Reductive Cleavage (DFRC)

A biomass sample, such as milled cell walls or isolated lignin (10-100 mg), and 1,1-bis-(4-hydroxyphenyl)ethane (BPA, 10-100 µg, an internal standard), are treated with an acetyl bromide:acetic acid solution (1/4 v/v, 0.4-4 mL) at 50° C. in a 2 dram vial with a PTFE pressure-release cap, gently stirring for 2.5 h. This step acetylates the free-phenolic and aliphatic hydroxyls, and brominates benzylic alcohols to produce benzylic bromides. (Treatment of coniferyl-ferulate diacetate model compound with acetyl bromide-acetic acid solution (1:4 v/v) at 50° C. for 2.5 h shows no evidence of transesterification as determined by GC-MS.) The solvent and reagents are removed on a Speed-Vac (Thermo Scientific SPD131DDA, 50° C., 35 min, 1.0 torr, 35 torr/min). The crude film is suspended in absolute ethanol (0.5 mL) and then the ethanol is removed on a SpeedVac (Thermo Scientific SPD131DDA, 50° C., 15 min, 6.0 torr, 35 torr/min). This quenches any residual acetyl bromide and also creates a phase transition in the brominated plant cell wall film. For the reductive cleavage step, the residue is suspended in dioxane/acetic acid/water (5/4/1 v/v, 5 mL). Nano-powder zinc (150 mg) is added to the suspension and then the vial is sealed, sonicated to ensure that the solids are suspended, and stirred in the dark at room temperature for 16-20 h. Additional nano-powder zinc is added as required to maintain a fine suspension of zinc.

The reaction is quantitatively transferred with dichloromethane (DCM, 6 mL) to a separatory funnel charged with dichloromethane (DCM, 10 mL), saturated ammonium chloride (10 mL), and internal standard(s) (10-200 µg of each). (Optimally, the set of internal standards includes spin-labeled derivatives of the monolignol and monolignol-conjugates of interest. FIG. 2 (rows 2 and 3) shows two sets of exemplary potential spin-labeled internal standards ($d_6$, $d_8$, and $d_{10}$). Table 1 provides MRM data for these standards.) The dichloromethane phase is collected and the aqueous phase is extracted again with dichloromethane (3×10 mL). The combined organic fraction is dried over sodium sulfate, filtered, and the solvent evaporated. The free hydroxyl groups are acetylated with pyridine/acetic anhydride (1/1 v/v, 5 mL) for 16 h, after which the solvent is removed to give a crude oily product. Additional or alternative steps to those described above are described by Lu et al. 1999 and Lu and Ralph 2014).

Solid-Phase Extraction (SPE) Clean-Up

To remove most of the polysaccharide-derived products, the crude DFRC products are quantitatively loaded onto an SPE cartridge (Supelco Supelclean LC-Si SPE tube, 3 mL, P/N: 505048) using dichloromethane (3×1 mL). The products are eluted with hexanes:EtOAc (1:1, 8 mL) and the combined solvents are removed on a rotary evaporator. The purified product mixture is quantitatively transferred to a GC-MS vial using dichloromethane and brought to a final solvent volume of 50-1000 µL.

GC-MS on a Basic Single-Quad System

The combined eluted solutions are concentrated to about 50-1000 µL; 1-5 µL is injected into the GC for GC-MS analysis. GC-MS is performed on a Shimadzu 2010plus GC-MS system using either scan mode (100-600 m/z) or selective-ion monitoring (SIM) mode with 3-4 representative daughter ions selected per compound. The GC injection port temperature is 250-260° C., the oven temperature program is: initial temp. 150° C. (hold 1 min), ramp at 10° C./min to 300° C., hold for 14 min.

GC-MS and Multiple Reaction Monitoring (MRM) on a Triple-Quad (TQ) System

Analyzing the samples on a GC-triple quadrupole (TQ)-MS provides greater confidence in the molecular identity of the ion of interest and improved signal-to-noise in the data. Therefore, the same samples can also be run on TQ-instrument, a Shimadzu GCMS-TQ8030 triple-quadrupole GC/MS/MS operating in multiple-reaction-monitoring (MRM) mode. The GC program and acquisition parameters, for both the DFRC products and the internal standards, are listed below in Table 1.

Figure 3A:
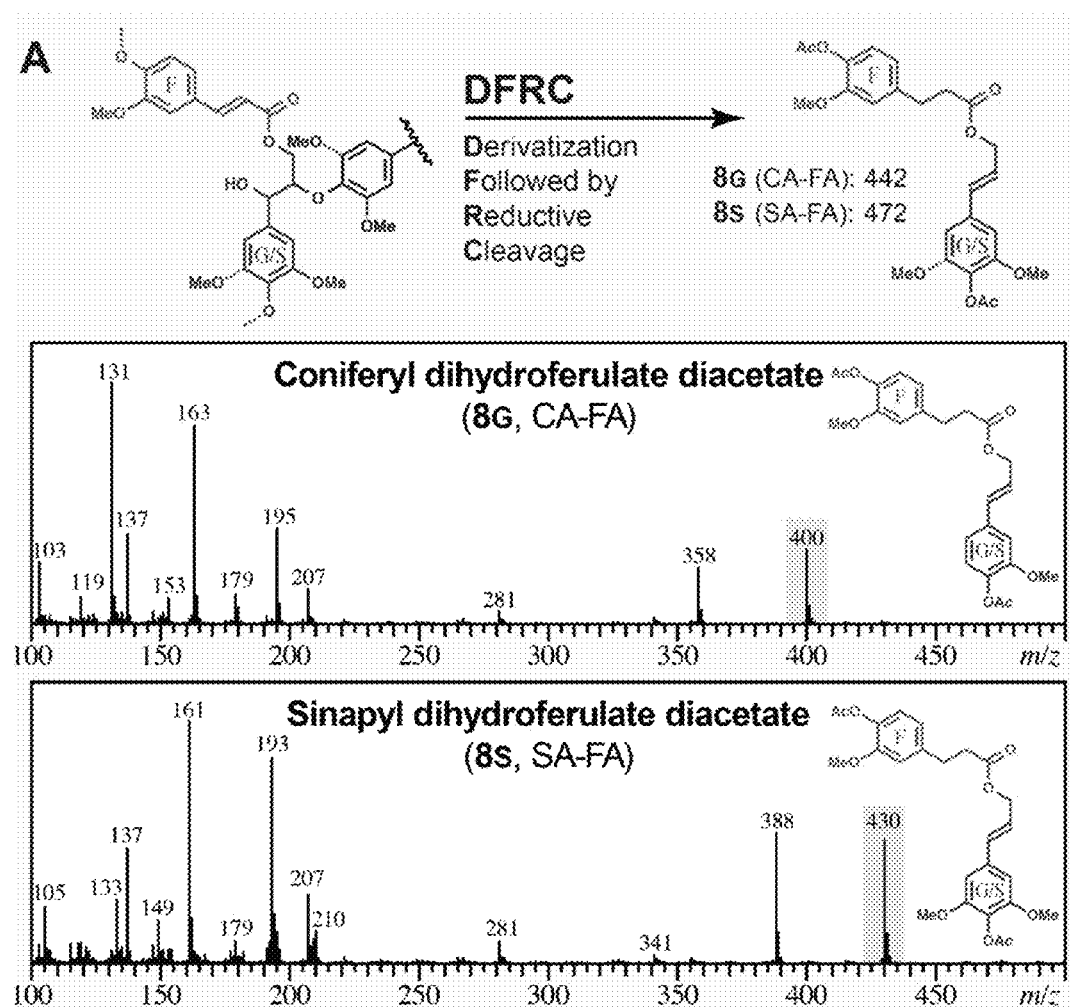
FIGS. 3A and 3B are mass spectrometric data showing incorporation of monolignol ferulate conjugates into lignin of transgenic CesA8::FMT-6 Poplar (Wilkerson et al. 2014) according to methods of the invention.
Figure 3B:
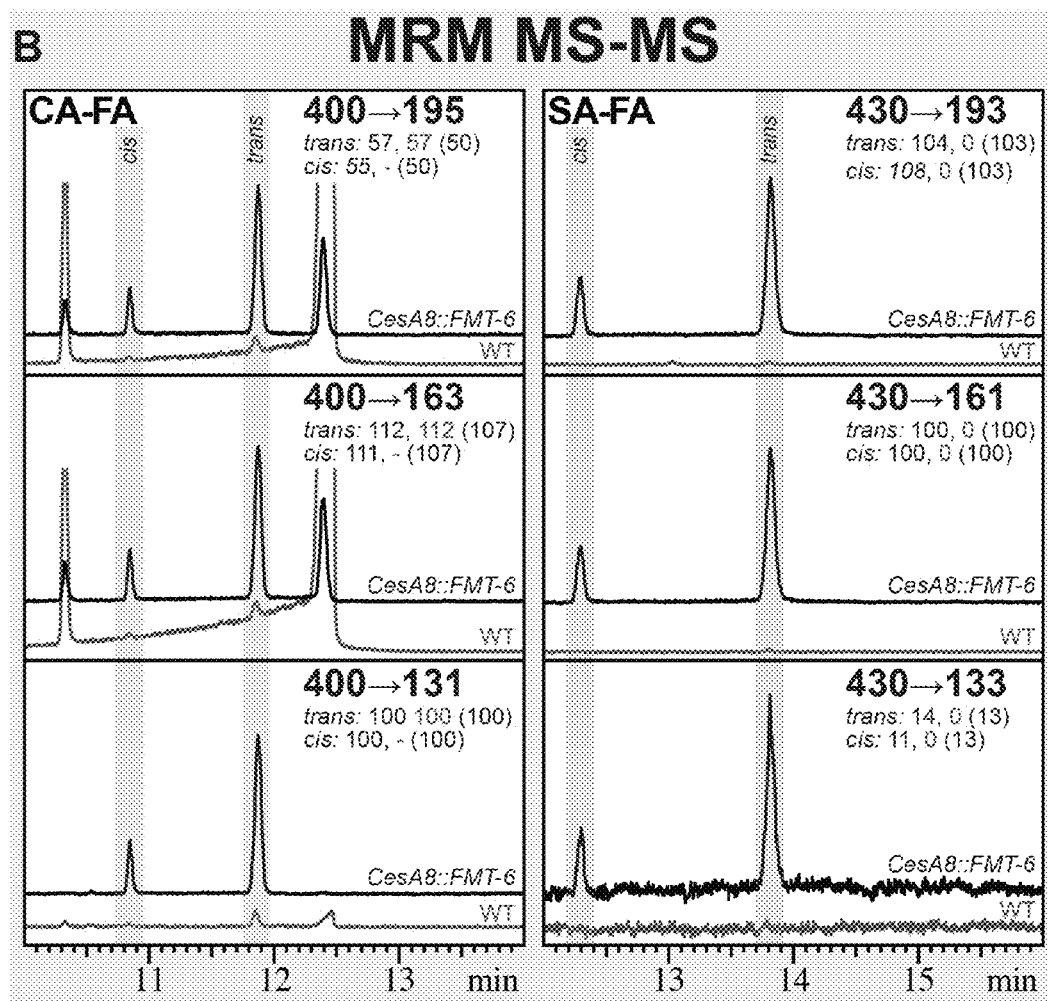
Figure 4A:
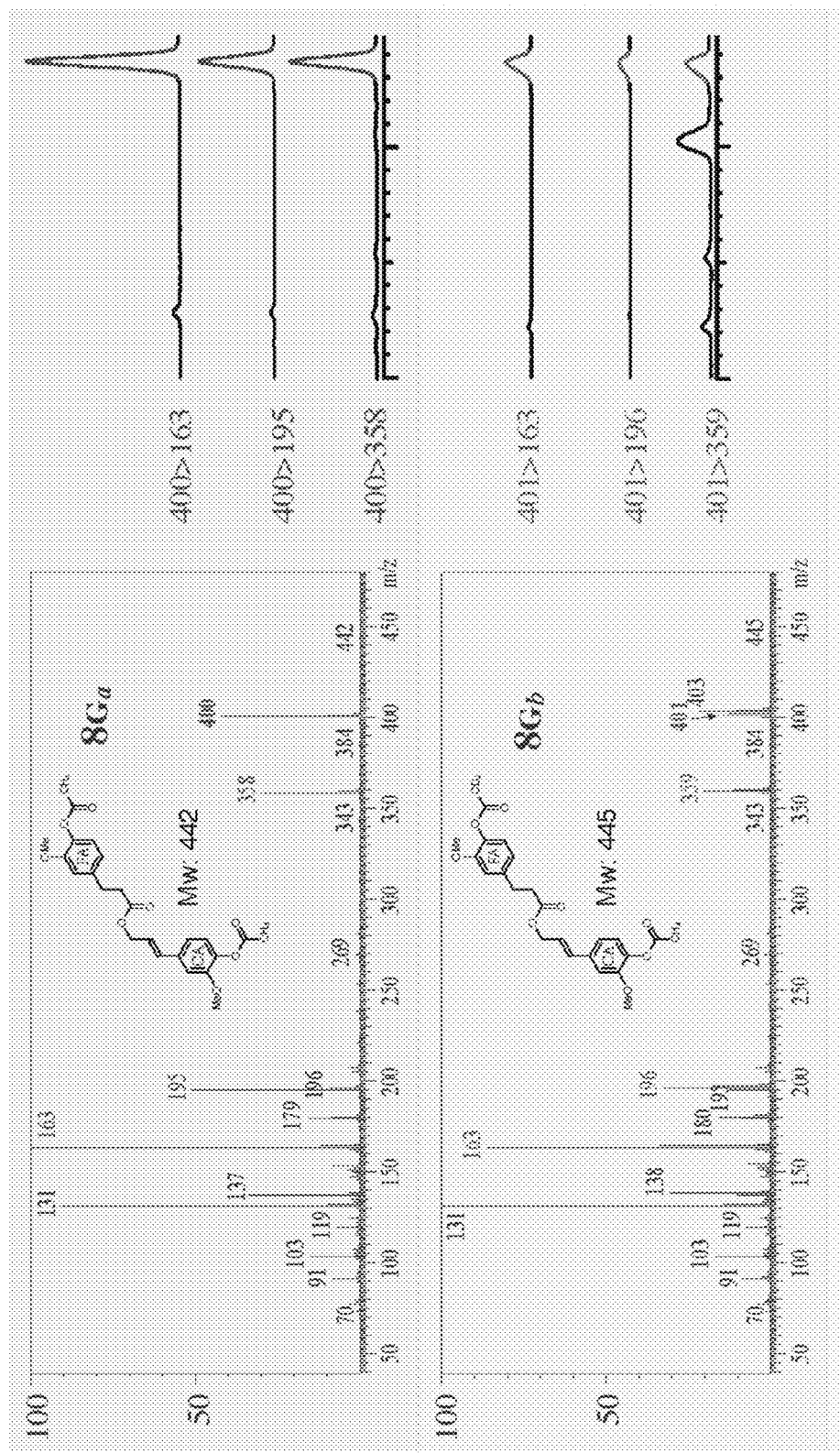
FIGS. 4A-4E show data from methods of using labeled reagents to determine etherification of ferulate conjugates. Left spectra in FIGS. 4A and 4B show mass spectra of synthetic and authentic compounds 8G$_a$ (FIG. 4A), 8G$_b$ (FIG. 4A), 8G$_e$ (FIG. 4B), and 8G$_d$ (FIG. 4B). Ions monitored by selective-ion monitoring (SIM) are colored and the MRM parents are shown in bold. Right spectra in FIGS. 4A and 4B show the presence of the expected differentially deuterated compounds 8G$_a$ (FIG. 4A) 8G$_b$ (FIG. 4A), 8G$_e$ (FIG. 4B), and 8G$_d$ (FIG. 4B).
Figure 4B:
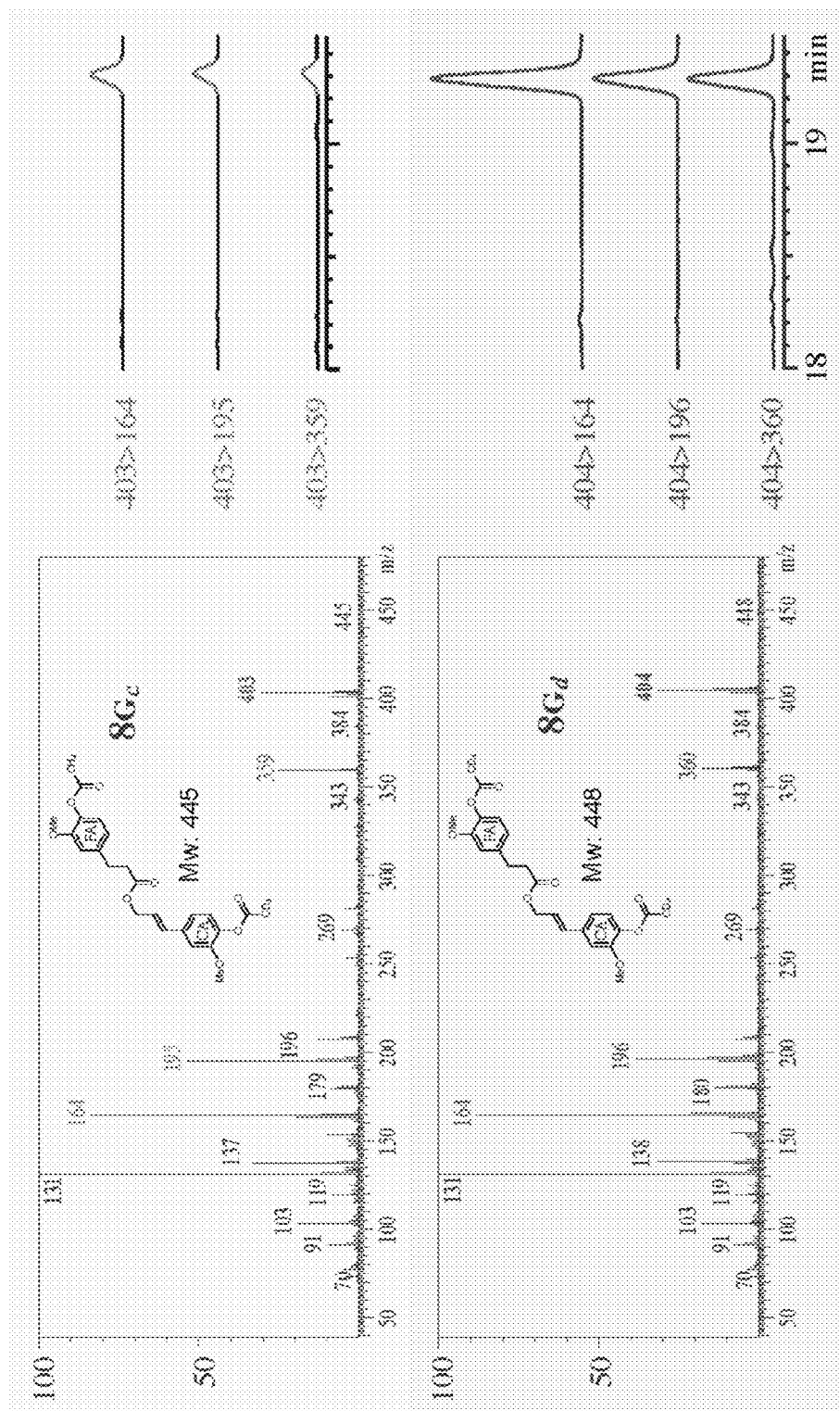
Figure 4C:
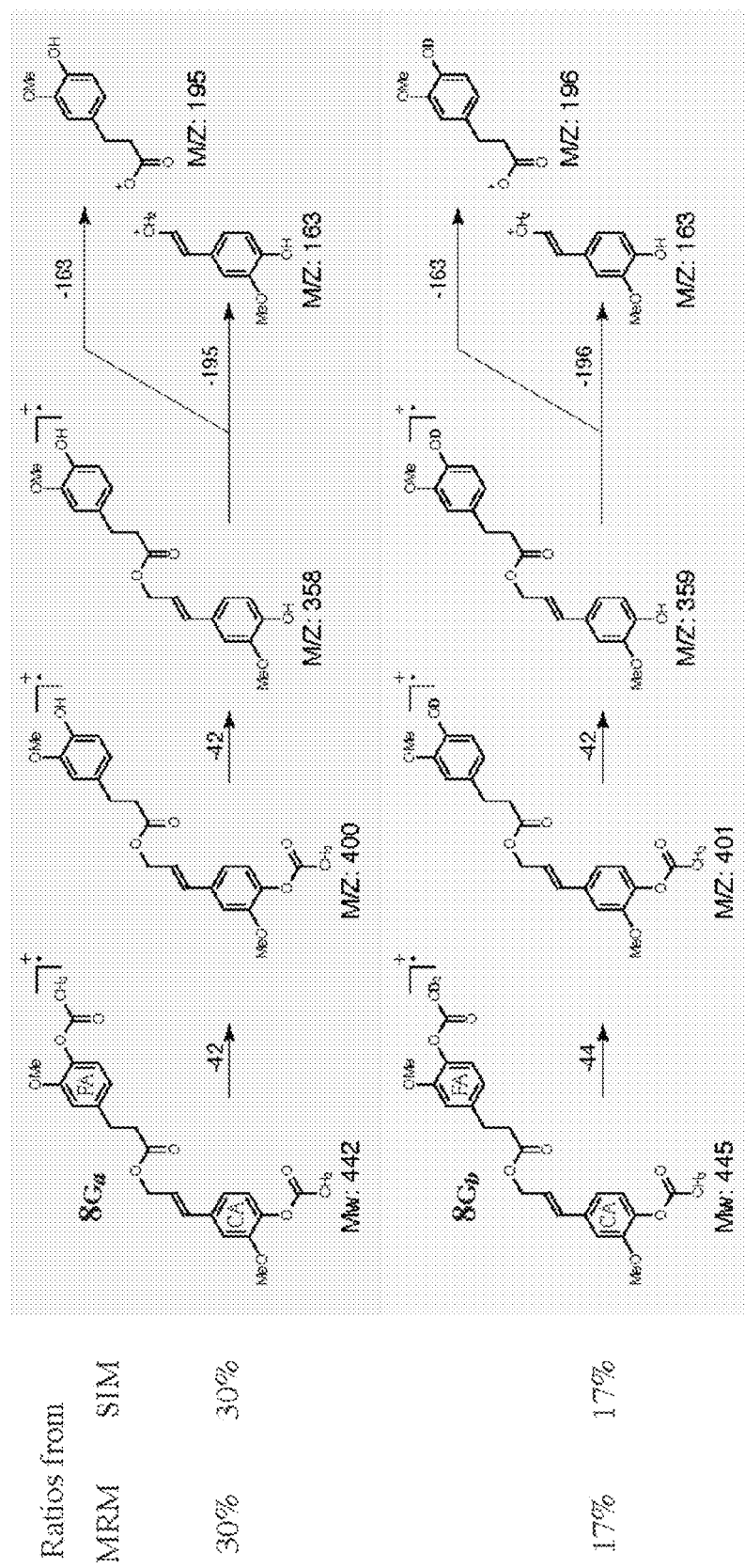
Figure 4D:
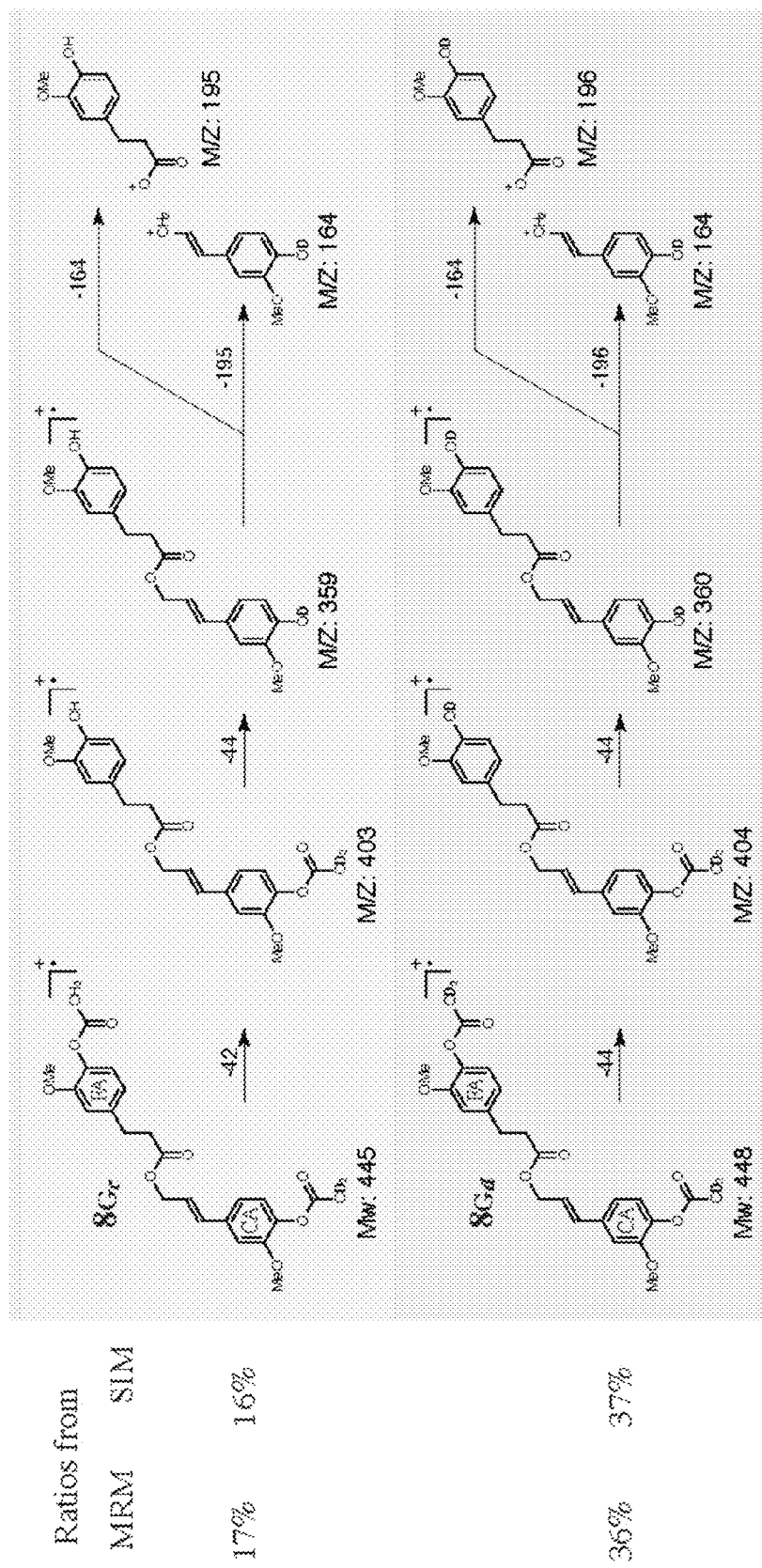
Figure 4E:
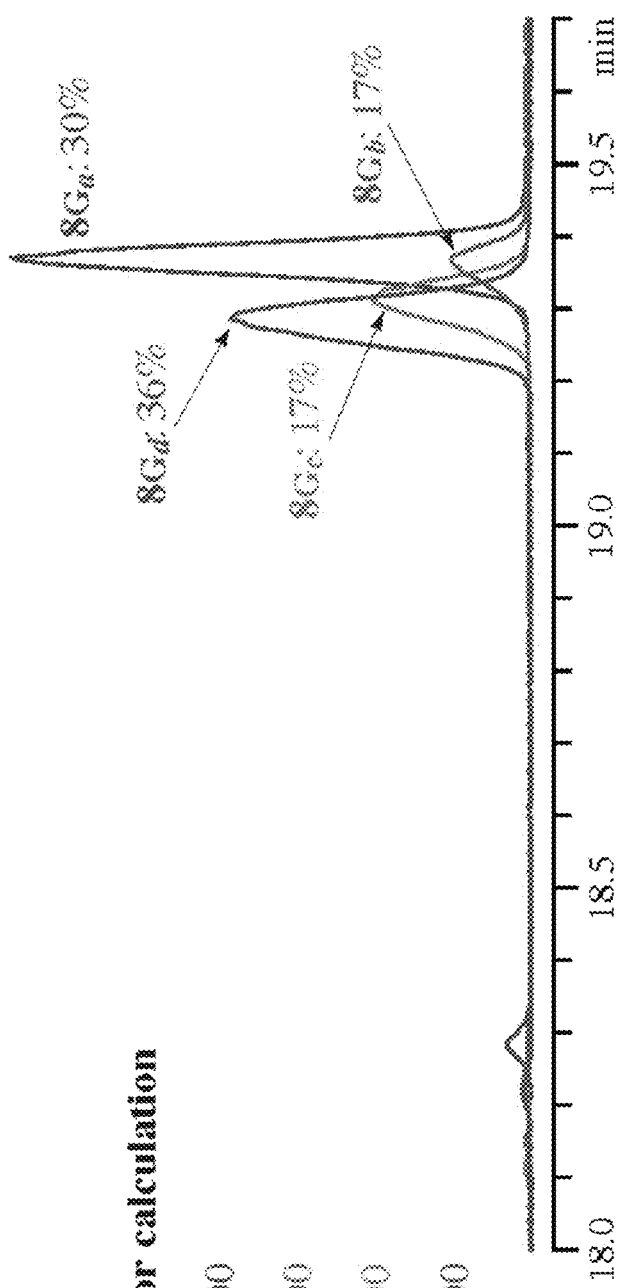

FIGS. 3A and 3B are mass spectrometric data showing incorporation of monolignol ferulate conjugates into lignin of CesA8::FMT-6 transgenic Poplar as described by Wilkerson et al. 2014.

FIG. 3A shows two of the products expected from DFRC treatment of the monolignol-ferulate-derived lignin. The upper mass spectrum in FIG. 3A is a Q3 ion scan of synthetic coniferyl dihydroferulate diacetate 8G (CA-FA, FIG. 1B and FIG. 3A) and the lower mass spectrum is for sinapyl dihydroferulate diacetate 8s (SA-FA, FIG. 1B and FIG. 3A). The ions with m/z=400 (highlighted in blue) for CA-FA and m/z=430 (highlighted in green) for SA-FA were then subjected to MRM.

FIG. 3B shows the chromatogram for the MRM transitions associated with CA-FA (left, 400→195, 400→163 and 400→131) and SA-FA (right, 430→193, 430→161 and 430→133), where the numbers besides the cis and trans labels are the ion ratios for the observed transitions relative to the 400→131 (CA-FA) or 430→161 (SA-FA) transition; they are reported from right to left as the ion ratio for CesA8::FMT-6 (black), WT (red), and in parenthesis the synthetic standard (showing that the data from the Poplar DFRC products also matches well with those of the authentic standard compounds).

The data in FIGS. 3A and 3B provide evidence of the release of the diagnostic conjugates from the lignin in transgenic Poplars and provide confirmation that the monolignol ferulate conjugates are transported intact to the lignifying zone (in the same fashion as the natural monolignol p-coumarate analogs in grasses) and are integrated, in the plant, into the lignin polymer. The data also provide evidence that the released DFRC conjugate 8G derives, in part, from units 5 (FIG. 1B) in which the phenolic ends of the coniferyl and the ferulate moiety are further etherified.

TABLE 1

Chromatography program and MRM parameters for GC/MS/MS characterization of DFRC product mix.

| | |
|---|---|
| Gas Chromatograph | GC-2010 Plus |
| Inlet | 250° C. |
| | Split liner with glass wool (Shimadzu 220-90784-00) |
| | Split injection (20:1) |
| Column | RXi-5Sil MS 30 m × 0.25 mm × 0.25 µm (Restek 13623) |
| | Helium carrier gas |
| | Constant linear velocity 45.0 cm/sec |
| Oven Program | 150° C., hold 1 min, ramp 10° C./minute to 300° C., hold 14 minutes |
| | MS interface 300° C. |
| | Analysis time 30 minutes |
| Mass Spectrometer | GCMS-TQ8030 |
| Ion Source | 250° C. |
| | Electron ionization (EI) mode, 70 eV |
| Operation Mode | Multiple Reaction Monitoring (MRM) |
| | Argon gas, 200 kPa |
| | Q1 resolution 0.8 u (Unit), Q3 resolution 0.8 u (Unit) |
| Detector | Electron multiplier |
| | 0.92 kV |

| MRM Transition Details | | | | | | | |
|---|---|---|---|---|---|---|---|
| Compound Name | Retention Time | Transition 1 | CE1 | Transition 2 | CE2 | Transition 3 | CE3 |
| p-coumaryl alcohol peracetate (HA) | 6.7 min 7.0 min | 234 > 196 | 6 | 234 > 150 | 14 | 234 > 149 | 14 |

TABLE 1-continued

Chromatography program and MRM parameters for GC/MS/MS characterization of DFRC product mix.

| Compound | RT | Q1 | CE1 | Q2 | CE2 | Q3 | CE3 |
|---|---|---|---|---|---|---|---|
| γ,γ-dideutero-p-coumaryl alcohol di-d₃-acetate (HA-d₈) | 6.7 min 7.0 min | 242 > 198 | 6 | 242 > 152 | 14 | 242 > 154 | 14 |
| coniferyl alcohol peracetate (CA) | 7.8 min 8.7 min | 264 > 222 | 6 | 264 > 179 | 14 | 264 > 124 | 26 |
| γ,γ-dideuteroconiferyl alcohol di-d₃-acetate (CA-d₈) | 7.8 min 8.7 min | 272 > 228 | 6 | 272 > 182 | 14 | 272 > 126 | 26 |
| sinapyl alcohol peracetate (SA) | 9.3 min 10.3 min | 294 > 256 | 6 | 294 > 161 | 26 | 294 > 149 | 26 |
| γ,γ-dideuterosinapyl alcohol di-d₃-acetate (SA-d₈) | 9.3 min 10.3 min | 302 > 258 | 6 | 302 > 163 | 20 | 302 > 151 | 26 |
| 1,1-bisphenoxyethane peracetate (BPA) | 11.3 min | 298→256 | 6 | 298→214 | 10 | 298→199 | 26 |
| 4-acetylconiferyl p-hydroxybenzoate-4-acetate (CA-pBz) | 17.1 min 17.3 min | 342→121 | 10 | 342→163 | 15 | 342→179 | 5 |
| 4-d₃-acetyl-γ,γ-dideutero coniferyl p-hydroxy-benzoate-4-d₃-acetate (CA*-pBz*-d₈) | 17.1 min 17.3 min | 348→122 | 5 | 348→166 | 15 | 348→182 | 10 |
| 4-acetylconiferyl 7,8-dihydro-p-coumaerate-4-acetate (CA-pCA) | 17.9 min 18.1 min | 370→131 | 22 | 370→179 | 10 | 370→163 | 14 |
| 4-d₃-acetyl-γ,γ-dideutero coniferyl 7,8-dideutero-p-coumaerate-4-d₃-acetate (CA*-pCA*-d₁₀) | 17.9 min 18.1 min | 377→133 | 22 | 377→182 | 10 | 377→166 | 14 |
| 4-acetylconiferyl 7,8-dihydroferulate-4-acetate (CA-FA) | 18.1 min 18.3 min | 400→163 | 14 | 400→131 | 26 | 358→163 | 10 |
| 4-d₃-acetylconiferyl 7,8-dihydroferulate-4-acetate (CA*-FA-d₃) | 19.4 min 19.6 min | 403→195 | 14 | 403→164 | 14 | 403→359 | 6 |
| 4-acetylconiferyl 7,8-dihydroferulate-4-d₃-acetate (CA-FA*-d₃) | 19.4 min 19.6 min | 401→196 | 14 | 401→163 | 14 | 401→359 | 6 |
| 4-d₃-acetylconiferyl 7,8-dihydroferulate-4-d₃-acetate (CA*-FA*-d₆) | 19.4 min 19.6 min | 404 > 131 | 26 | 404 > 164 | 14 | 360 > 164 | 10 |
| 4-d₃-acetyl-γ,γ-dideuteroconiferyl 7,8-dideuteroferulate-4-d₃-acetate (CA*-FA*-d₁₀) | 19.4 min 19.6 min | 408 > 133 | 26 | 408 > 166 | 14 | 364 > 166 | 10 |
| 4-acetylsinapyl p-hydroxybenzoate-4-acetate (SA-pBz) | 18.7 min 18.9 min | 372→121 | 10 | 372→163 | 15 | 372→209 | 10 |
| 4-d₃-acetyl-γ,γ-dideutero sinapyl p-hydroxy-benzoate-4-d₃-acetate (SA*-pBz*-d₈) | 18.7 min 18.9 min | 378→122 | 5 | 378→166 | 15 | 378→212 | 10 |
| 4-acetylsinapyl 7,8-dihydro-p-coumaerate-4-acetate (SA-pCA) | 19.5 min 19.8 min | 400→161 | 18 | 400→193 | 14 | 400→149 | 18 |
| 4-d₃-acetyl-γ,γ-dideutero sinapyl 7,8-dideutero-p-coumaerate-4-d₃-acetate (CA*-pCA*-d₁₀) | 19.5 min 19.8 min | 407→163 | 18 | 407→196 | 14 | 407→151 | 18 |
| 4-acetylsinapyl dihydroferulate-4-acetate (SA-FA) | 19.7 min 21.2 min | 430→193 | 14 | 430→161 | 26 | 388→161 | 22 |
| 4-d₃-acetylsinapyl 7,8-dihydroferulate-4-d₃-acetate (SA*-FA*-d₆) | 19.7 min 21.2 min | 434→194 | 14 | 434→161 | 26 | 390→161 | 22 |

TABLE 1-continued

Chromatography program and MRM parameters for GC/MS/MS characterization of DFRC product mix.

| | | | | | | | | |
|---|---|---|---|---|---|---|---|---|
| 4-d$_3$-acetyl-γ,γ-dideuterosinapyl 7,8-dideuteroferulate-4-d$_3$-acetate (SA*-FA*-d$_{10}$) | 19.7 min 21.2 min | 437→196 | 14 | 437→163 | 26 | 393→164 | 10 |
| 4-acetylconiferyl 7,8-dihydrosinapate-4-acetate (CA-SA) | 21.1 min 21.4 min | 430→163 | 14 | 430→225 | 14 | 388→131 | 26 |
| 4-d$_3$-acetyl-γ,γ-dideutero coniferyl 7,8-dideutero-sinapate-4-d$_3$-acetate (CA*-SA*-d$_{10}$) | 21.1 min 21.4 min | 437→166 | 14 | 437→133 | 14 | 393→227 | 6 |
| 4-acetylsinapyl 7,8-dihydrosinapate-4-acetate (SA-SA) | 23.7 min 24.0 min | 460→161 | 26 | 460→418 | 10 | 418→161 | 22 |
| 4-d$_3$-acetyl-γ,γ-dideutero sinapyl 7,8-dideutero-sinapate-4-d$_3$-acetate (SA*-SA*-d$_{10}$) | 23.7 min 24.0 min | 467→164 | 26 | 467→423 | 5 | 423→196 | 15 |
| diethyl 5,5'-diferulate peracetate (DEDF)* | 15.81 min | 484→442 | 6 | 484→396 | 14 | 484→350 | 18 |

Determination of Whether Ferulate-8-O-4-Aryl Ethers Cleave Under DFRC

The compounds in which the ferulate undergoes 8-O-4-coupling with a phenol produces a special β-ether structure with 7,8-unsaturation. This arises because the intermediate quinone methide is re-aromatized by the loss of the acidic β-proton rather than by trapping via external water. It is not a priori clear whether these bonds will cleave during DFRC. Subjecting a good model for all of these compounds, e.g., the 8-O-4-coupled dehydrodiferulate (dimer), to DFRC does not result in cleavage of the β-ether bond at all (and consequently released no ferulate monomer derivatives). Thus, the set of compounds that can release the conjugate are the guaiacyl-comprising compounds presented immediately below and analogous compounds comprising p-hydroxyphenyl and syringyl units:

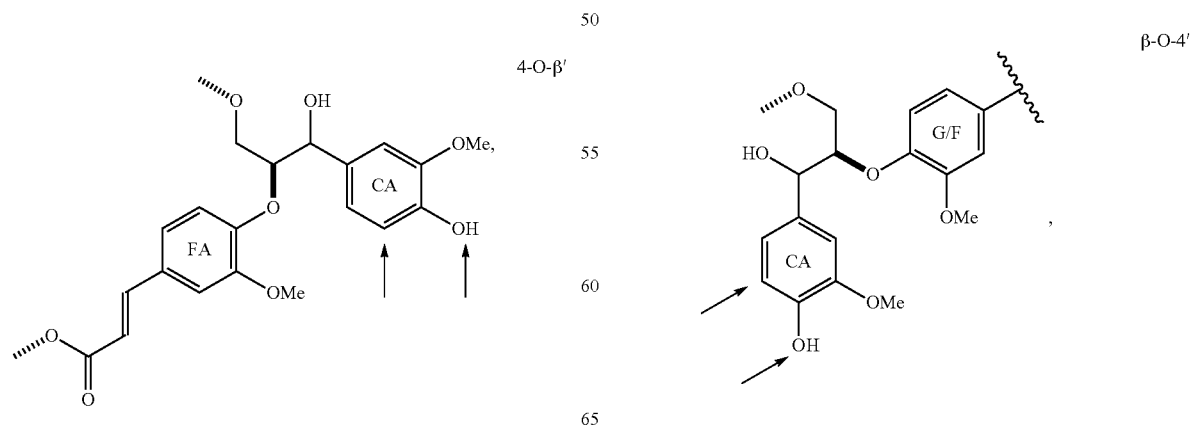

-continued

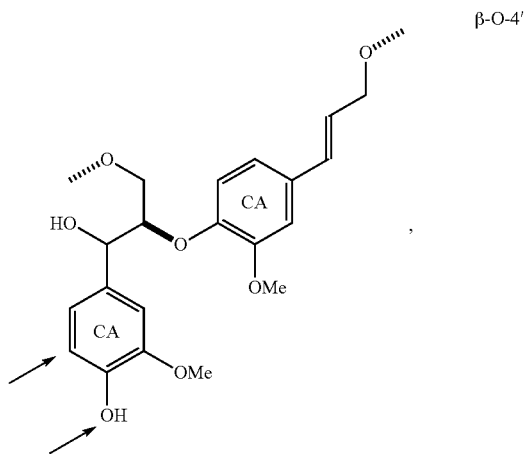

-continued

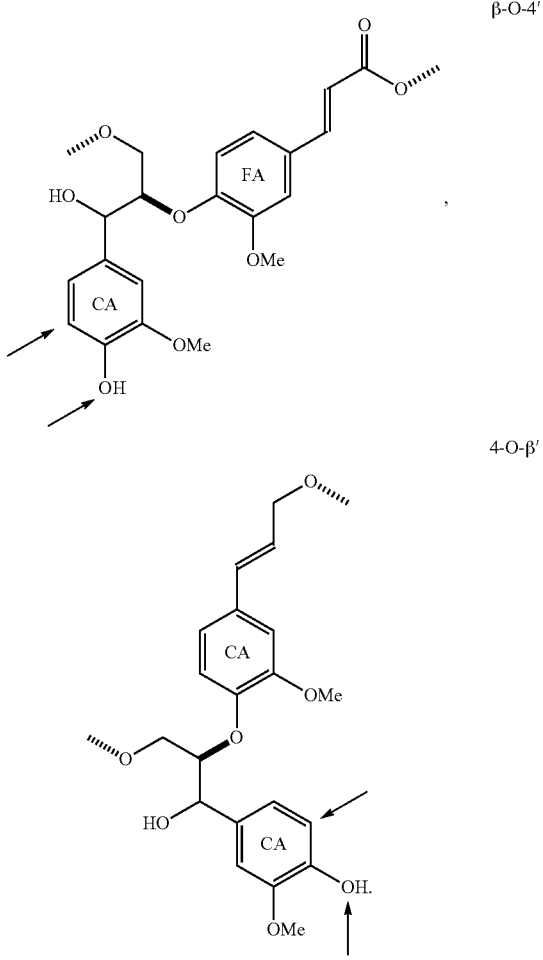

Using Labeled Reagents to Determine the Etherification State of DFRC-Released Conjugates A labeled acetylation reagent can be used to discriminate between those units that, in the polymer, were originally etherified vs. free-phenolic units (see FIG. 1B). By utilizing perdeuteroacetic anhydride or another labeled acetylation reagent in the final acetylation step, the originally-etherified units are "tagged" with a label. A feature of this method is that the etherification level is, at best, underestimated. An alternative method in which lignins are first methylated and then subjected to DFRC or thioacidolysis likely overestimates the etherification level as any phenolics not methylated will analyze as etherified units. (This scenario is easy to envision due to the difficulty of completely methylating cell wall polymers by diazomethane, even by the exhaustive, two-week, methylation). In the present method, all possible etherification states are distinguishable and quantifiable by MS in accordance with the parameters shown in Table 1. The possible etherification states include: β-etherification only with no monolignol unit etherification and no phenolic carboxylate unit etherification, phenolic carboxylate unit etherification with no monolignol unit etherification, monolignol unit etherification with no phenolic carboxylate unit etherification, and phenolic carboxylate unit etherification with monolignol unit etherification. No transacetylation occurs under the pyridine/acetic anhydride reaction conditions.

Mass spectra of the labeled standards (such as deuterium-labeled standards) can be acquired on a Shimadzu 2010plus GC-MS (EI) single-quad instrument run in both scan mode and SIM mode. The MRM analysis of the labeled standards can be performed on a Shimadzu GCMS-TQ8030 triple quadrupole GC/MS/MS.

In accordance with the above-described method, CesA8:: FMT-6 transgenic Poplar wood (Wilkerson et al. 2014, including supplementary information) (600 mg, ground and extracted) was stirred in 15 mL AcBr-HOAc (12 mL HOAc and 3 mL AcBr) in a round bottom flask placed in a sand bath at 50° C. for 3.5 h. After evaporating all liquids completely under reduced pressure on a rotary evaporator, the residue (light brown syrup) was dissolved in dioxane-acetic acid-water (8 mL, 5/4/1, v/v/v); while stirring the mixture well, 950 mg Zn dust were added. Stirring was continued for 40 min. Following the normal workup (dichloromethane extraction, see above), the residues were acetylated with 0.5 g $Ac_2O-d_6$/0.5 g pyridine in 5 mL dichloromethane for 1 h. After adding 5 mL ethanol, the solution was evaporated under reduced pressure via a rotary evaporator. This operation was repeated several times until all acetic acid and pyridine were totally removed.

The crude DFRC products were dissolved in dichloromethane (1.5 mL) and then precipitated with absolute ethanol (40 mL) to remove excess polysaccharide-derived components. After centrifugation, the solvent was removed from the supernatant. The residues were loaded with 1 mL dichloromethane onto a Biotage snap silica gel column (25 g silica) and eluted with hexane/ethyl acetate (EtOAc) on a Biotage flash chromatography instrument (Isolera One) with UV detector and auto-collector, eluting sequence: 10% EtOAc (150 mL), 15% EtOAc (700 mL), 25% EtOAc (270 mL), 33% EtOAc (140 mL), 50% EtOAc (120 mL). Fractions (from eluting volume 1000-1300 mL) were collected and evaporated to give a pale colored oil. The resulting oily products were dissolved in 0.25 mL dichloromethane for GC-MS analysis. Spectra are shown in FIGS. 4A-E.

As shown in FIGS. 4A-E, 53% of the ferulate and 53% of the coniferyl alcohol moieties in the releasable conjugates were from phenol-etherified units, and 36% resulted from units that have both ends of the conjugate etherified. Because only a small fraction of units can release the conjugate, and further because the double bond in the coniferyl alcohol moiety implies that it is derived from a β-etherified unit, an etherified phenolic level comparable to that of the released guaiacyl monomers (determined in the same runs at ~50%) confirms that the conjugate is incorporated into the lignin polymer approximately as well as a conventional monolignol.

Method to Estimate the Monolignol Ferulate Incorporation Level

As a means to estimate the amount of monolignol ferulate conjugates 2G/2s (FIG. 1A) that incorporated into lignin structure, a model system with known levels of ferulate incorporation on a weight-percent lignin basis was studied. A series of synthetic cell wall lignins were prepared from suspensions of maize cell walls by feeding them a 1:1 mixture of coniferyl alcohol 1G and sinapyl alcohol 1s (FIG. 1A) with either coniferyl ferulate 2G (0, 8.4, 15.4, 26.7 wt %) or sinapyl ferulate 2s (0, 9.0, 16.5, 28.4 wt %) in a 30% dioxane:water solution (1). The cell wall DHPs were then analyzed by DFRC following the procedure detailed above, and the results were plotted as the wt % monolignol dihydroferulate (ML-DHFA) released per gram of acetyl bromide lignin vs. wt % monolignol ferulate used to prepare the cell wall dehydrogenation polymers (DHPs). See Table 2.

Regression constants for the released monolignol dihydroferulates were determined by fitting the data to a linear model (y=mx, y=wt % monolignol dihydroferulate in cell wall DHP; x=wt % monolignol dihydroferulate released; 4-acetylconiferyl dihydroferulate-4-acetate (CA-FA): m=53, $R^2$=0.99; 4-acetylsinapyl dihydroferulate-4-acetate (SA-FA): m=34, $R^2$=0.99). The result from this series of maize cell wall DHPs confirms a direct correlation between DFRC-releasable monolignol dihydroferulate-conjugates and the amount of monolignol ferulate used to prepare the DHPs. This is a relative scale for making comparisons about the level of ferulate incorporation and estimating the amount of ferulate incorporation.

TABLE 2

Levels of DFRC released monolignol-conjugates 8.

| Weight percent ML-FA used to prepare the cell wall DHP | Detected CA-DHFA (wt % of AcBr lignin) | Detected SA-DHFA (wt % of AcBr lignin) |
|---|---|---|
| ML-FA (0%) | 0.0% | 0% |
| CA-FA (8%) | 0.2% | 0% |
| CA-FA (15%) | 0.3% | 0% |
| CA-FA (27%) | 0.5% | 0% |
| SA-FA (9%) | 0% | 0.3% |
| SA-FA (17%) | 0% | 0.5% |
| SA-FA (28%) | 0% | 0.9% |
| CA-FA (8%), SA-FA (8%) | 0.2% | 0.2% |

"ML-FA" = monolignol ferulates 2G/2S (FIG. 1A).
"CA-FA" = 4-acetylconiferyl dihydroferulate-4-acetate.
"SA-FA" = 4-acetylsinapyl dihydroferulate-4-acetate.
"CA-DHFA" = 8G and "SA-DHFA" = 8S, these are the DFRC released products of monolignol ferulates incorporated into the cell wall DHPs that are detected by GC-MS.

For estimating the amount of ferulate conjugates 2 incorporated into the lignin of the CesA8::FMT Poplar trees (Wilkerson et al. 2014), a model system similar to that outlined above was made in which isolated cell walls were ectopically lignified with coniferyl alcohol and 0, 20, 40, and 60% coniferyl ferulate (Grabber et al. 2008). By plotting the release of the DFRC conjugates in the model system and those released from the current transgenic lines, it was estimated that the CesA8::FMT Poplar trees incorporated about 7 to about 23% of the ferulate conjugates 2 into their lignins.

Exemplary Protocol for DFRC of Whole Plant Cell Walls to Quantify Incorporation of Monolignols and Monolignol Ferulate Conjugates Therein A. Cell Wall Sample Preparation
  1. Air-dry plant stems: sticks or Wiley milled cell walls to pass through a 40 mesh screen
  2. Cut the sample into small pieces (10 mm×2 mm)
  3. Pre-grind the sample so it passes a 1 mm mesh screen. Do not over-grind! For the most reproducible results, prepare the samples to a uniform particle size.
  4. Remove solvent-extractable Components
    4.1. Add cell wall samples (<2 g) to a 50 mL centrifuge tube
      4.1.1. Add 40 mL of 80% ethanol
      4.1.2. Sonicate for 20 min.
      4.1.3. Centrifuge (10 min. @ less than ~50,000 xG for PPCO tube, Sorval biofuge primo; 8,500 rpm or 10,016×G); decant solvent
      4.1.4. Repeat 3 times
      4.1.5. Cover the sample with a Kimwipe and secured it with a rubber band.
      4.1.6. Place the sample in a fume hood until roughly dry, usually 24-48 hours.
  5. Dry the samples in a freeze-dryer for 48 hours.

B. Bromination of α-Carbons
  Reagents: Brominating solution: 20% acetyl bromide in glacial acetic acid (freshly prepare) BPO solution: 1,1-bis (4-hydroxyphenyl)ethane in EtOAc 2.00 mg/mL Vial: Fisher 50-872-8002 or Chemglass Inc. CG 4912-02
  1. Weigh out the extracted cell wall (CW) or isolated lignin sample (20-50 mg) on a micro-balance and transfer it to a 2-dram vial with a PTFE pressure relief cap and a small Teflon stir bar.
  2. Spike the reaction with a 100 µg BPO (50 µL of 2.00 mg/mL in EtOAc) recovery standard.
  3. In a fume hood, add to the vial 0.5 mL of brominating solution for every 10 mg sample. Note: The solution should smoke in the air.
  4. Place the vial in a 50° C. sand bath. Stirring continuously, heat the reaction for 2.5 hours.
  5. After heating, remove the solvent on a Speedvac (Thermo Scientific SPD131DDA, 50° C., 35 min, 1.0 torr, 35 torr/min).
  6. Quench the residual acetyl bromide with absolute ethanol (0.5 mL).
  7. Remove the ethanol on a SpeedVac (50° C., 15 min, 6.0 torr, 35 torr/min). The residual will typically be a light to dark orange/brown film.

C. Zinc Reduction
  Reagents: Zinc—nano-powder.
  Reduction solution: dioxane:acetic acid:water [5:4:1]
  5,5'-DEDF solution: Diethyl 5,5'-diferulate-peracetate in EtOAc 1.00 mg/mL
  1. Once all of the ethanol solution is evaporated to give a film, add 5 mL of the reduction solution and nano-powder zinc (125 mg) to the vial and cap was returned to the vial.
  2. Sonicate the reaction to ensure fine suspension.
  3. Stir the reaction in the dark at room temperature for 16-20 hours, adding additional nano-powder zinc as required to maintain a fine suspension. Note: There should be bubbles forming from zinc reacting with the acetic acid.
  4. Charge a 60 mL separatory funnel with sat. $NH_4Cl$ (10 mL), dichloromethane (10 mL), and recovery standard DEDF (50 µg, 50 µL of 1.00 mg/mL in EtOAc).
  5. Quantitatively transfer the reduction crude to the charged separatory funnel using dichloromethane (3×2 mL) and collected the organic fraction (bottom).
  6. Extract all of the organics from the aqueous layer (top) with dichloromethane (bottom) (3×10 mL).
  7. Combined the organic fractions and dry them over anhydrous sodium sulfate.
  8. Filter off the drying agent and removed the solvent on a rotovap (water bath at <50° C.).

D. Acetylation of Free Hydroxyls
  1. Dissolve the reduction crude product in a 1:1 mixture of pyridine and acetic anhydride (5 mL).
  2. Seal the flask and place in the dark overnight.
  3. Remove the solvent on a rotovap, heating the water bath to 50° C., this typically results in an orange/brown film.

E. Purification of Crude Product
  Solid Support: Supelco filter: Supelclean LC-SI, 3 mL tubes, P/N 505048.
  1. Transfer the acetylated film to a SPE cartridge Supelco (Supelco Supelclean LC-Si SPE tube, 3 mL, P/N: 505048) using dichloromethane (3×1 mL).
  2. Elute the product with a 1:1 solution of hexanes and ethyl acetate (8 mL), apply mild pressure with a Teflon plunger. This produces a light yellow solution.

3. Combine the eluted solutions and removed the solvent on rotovap (water bath at <50° C.).

F. GC-MS Analysis
 1. Dissolve the purified sample in dichloromethane (1 mL) and transfer this solution to a GC vial (1.5 mL amber vial from Supelco), and seal the vial using a PFTE/Silicone cap.
 2. Analyze the product mixture on either a GC-MS or GC-MRM-MS
 3. The preferred column is an Agilent DB-1701 (14% cyanopropyl-phenyl and 86% methylpolysiloxane), RESTEK RX1-5 ms (5% diphenylsilyl and 95% dimethylsilyl), or DB-1 (100% dimethylsilyl fused silica solid supports).

REFERENCES

L. E. Bartley et al., Overexpression of a BAHD acyltransferase, OsAt10, alters rice cell wall hydroxycinnamic acid content and saccharification. *Plant Physiol* 161, 1615 (2013).

W. Boerjan, J. Ralph, M. Baucher, Lignin biosynthesis. *Annu. Rev. Plant Biol.* 54, 519 (2003).

N. D. Bonawitz et al., Disruption of the transcriptional coregulatory complex Mediator rescues the stunted growth of a lignin-deficient *Arabidopsis* mutant. *Nature*, in press (2014).

H.-M. Chang, E. B. Cowling, W. Brown, E. Adler, G. Miksche, Comparative studies on cellulolytic enzyme lignin and milled wood lignin of sweetgum and spruce. *Holzforschung* 29, 153 (1975).

F. Chen, R. A. Dixon, Lignin modification improves fermentable sugar yields for biofuel production. *Nature Biotechnol.* 25, 759 (2007).

F. Chen, Y. Tobimatsu, D. Havkin-Frenkel, R. A. Dixon, J. Ralph, A polymer of caffeyl alcohol in plant seeds. *Proc. Natl. Acad. Sci.* 109, 1772 (2012).

H. D. Coleman, J.-Y. Park, R. Nair, C. Chapple, S. D. Mansfield, RNAi-mediated suppression of p-coumaroyl-CoA 3'-hydroxylase in hybrid poplar impacts lignin deposition and soluble secondary metabolism. *Proc. Natl. Acad. Sci.* 105, 4501 (2008).

T. P. Durrett et al., A distinct DGAT with sn-3 acetyltransferase activity that synthesizes unusual, reduced-viscosity oils in *Euonymus* and transgenic seeds. *Proc. Natl. Acad. Sci.* 107, 9464 (2010).

R. C. Edgar, MUSCLE: multiple sequence alignment with high accuracy and high throughput. *Nucleic Acids Res* 32, 1792 (2004).

J. H. Grabber, R. D. Hatfield, F. Lu, J. Ralph, Coniferyl ferulate incorporation into lignin enhances the alkaline delignification and enzymatic degradation of maize cell walls. *Biomacromolecules* 9, 2510 (2008).

D. H. Huson et al., Dendroscope: An interactive viewer for large phylogenetic trees. *Bmc Bioinformatics* 8, 460 (2007).

M. Karimi, B. De Meyer, P. Hilson, Modular cloning in plant cells. *Trends Plant Sci.* 10, 103 (2005).

N. Kolosova et al., Isolation of high-quality RNA from gymnosperm and angiosperm trees. *Biotechniques* 36, 821 (2004).

E. Y. Li et al., The Class II KNOX gene KNAT7 negatively regulates secondary wall formation in *Arabidopsis* and is functionally conserved in *Populus. New Phytologist* 194, 102 (2012).

X. Li, J. K. Weng, C. Chapple, Improvement of biomass through lignin modification. *Plant J.* 54, 569 (2008).

F. Lu, J. Ralph, Detection and determination of p-coumaroylated units in lignins. *J. Agr. Food Chem.* 47, 1988 (1999).

F. Lu, J. Ralph, The DFRC (Derivatization Followed by Reductive Cleavage) method and its applications for lignin characterization. in *Lignin: Structural Analysis, Applications in Biomaterials, and Ecological Significance*, F. Lu, Ed. (Nova Science Publishers, Inc, Hauppauge, N.Y., USA, 2014), in press.

P. T. Martone et al., Discovery of lignin in seaweed reveals convergent evolution of cell-wall architecture. *Current Biology* 19, 169 (2009).

D. Petrik et al., p-Coumaroyl-CoA:Monolignol Transferase (PMT) acts specifically in the lignin biosynthetic pathway in *Brachypodium distachyon. Plant J.*, in press (accepted Dec. 17, 2013) (2014).

J. Ralph, Lundquist, K., Brunow, G. Lu, F., Kim, H., Schatz, P. F., Marita, J. M., Hatfield, R. D., Ralph, S. A. Christensen, J. H., Boerjan, W., Lignins: natural polymers from oxidative coupling of 4-hydroxyphenylpropanoids. *Phytochem. Revs.* 3, 29 (2004).

J. Ralph et al., Lignification: Are lignins biosynthesized via simple combinatorial chemistry or via proteinaceous control and template replication? in *Recent Advances in Polyphenol Research, Vol* 1, F. Daayf, A. El Hadrami, L. Adam, G. M. Ballance, Eds. (Wiley-Blackwell Publishing, Oxford, U K, 2008), vol. 1, pp. 36-66.

J. Ralph, Hydroxycinnamates in Lignification. *Phytochem. Revs.* 9, 65 (2010).

A. R. Robinson, S. D. Mansfield, Rapid analysis of poplar lignin monomer composition by a streamlined thioacidolysis procedure and near-infrared reflectance-based prediction modeling. *Plant J.* 58, 706 (2009).

N. Santoro et al., A high-throughput platform for screening milligram quantities of plant biomass for lignocellulose digestibility. *Bioenergy Research* 3, 93 (2010).

H. A. Schmidt, K. Strimmer, M. Vingron, A. von Haeseler, TREE-PUZZLE: maximum likelihood phylogenetic analysis using quartets and parallel computing. *Bioinformatics* 18, 502 (2002).

J. J. Stewart, T. Akiyama, C. C. S. Chapple, J. Ralph, S. D. Mansfield, The effects on lignin structure of overexpression of ferulate 5-hydroxylase in hybrid Poplar. *Plant Physiol.* 150, 621 (2009).

C. Subramanian et al., A suite of tools and application notes for in vivo protein interaction assays using bioluminescence resonance energy transfer (BRET). *Plant J.* 48, 138 (2006).

R. Vanholme, K. Morreel, J. Ralph, W. Boerjan, Lignin engineering. *Curr. Opin. Plant Biol.* 11, 278 (2008).

R. Vanholme et al., Engineering traditional monolignols out of lignins by concomitant up-regulation F5H1 and down-regulation of COMT in *Arabidopsis Plant J.* 64, 885 (2010).

R. Vanholme et al., Metabolic engineering of novel lignin in biomass crops. *New Phytologist* 196, 978 (2012).

R. Vanholme et al., Caffeoyl shikimate esterase (CSE), a newly discovered gene in the lignin biosynthetic pathway. *Science* 341, 1103 (2013).

A. Wagner et al., Exploring lignification in conifers by silencing hydroxycinnamoyl-CoA:shikimate hydroxycinnamoyltransferase in *Pinus radiata. Proc. Natl. Acad. Sci.* 104, 11856 (2007).

J.-K. Weng, H. Mo, C. Chapple, Over-expression of F5H in COMT-deficient *Arabidopsis* leads to enrichment of an unusual lignin and disruption of pollen wall formation. *Plant J.* 64, 898 (2010).

S. Withers et al., Identification of a grass-specific enzyme that acylates monolignols with p-coumarate. *J. Biol. Chem.* 287, 8347 (2012).

J. J. Xie et al., Optimization and comparison of five methods for extraction of coniferyl ferulate from *Angelica sinensis*. *Molecules* 14, 555 (2009).

Q. Zhao et al., Loss of function of Cinnamyl Alcohol Dehydrogenase 1 causes accumulation of an unconventional lignin and a temperature-sensitive growth defect in *Medicago truncatula*. *Proc. Natl. Acad. Sci.* 110, 13660 (2013).

Y. Zhu et al., Preparation of monolignol γ-acetate, γ-p-hydroxycinnamate, and γ-p-hydroxybenzoate conjugates: Selective deacylation of phenolic acetates with hydrazine acetate. *RSC Advances* 3, 21964 (2013).

What is claimed is:

1. A method of detecting and, optionally, determining a level of incorporation of monolignol ester conjugates into lignin, the method comprising:
   (a) derivatizing lignin to acylate at least a portion free phenolic and aliphatic hydroxyls and to halogenate at least a portion of benzylic alcohols present in the lignin, to yield derivatized lignin;
   (b) treating the derivatized lignin of step (a) with a reducing agent to cleave at least a portion of the derivatized lignin, to yield lignin cleavage products;
   (c) acetylating at least a portion of free hydroxyl groups in the lignin cleavage products of step (b) with a labeled acetylation agent, to yield labeled lignin fragments, wherein the labeled acetylation agent is labeled acetic anhydride, wherein the labeled acetic anhydride is labeled with an isotope; and
   (d) detecting the labeled lignin fragments produced in step (c), wherein the detecting the labeled lignin fragments comprises:
      isolating the labeled lignin fragments, wherein each lignin fragment comprises a monolignol ester conjugate, wherein each monolignol ester conjugate comprises a monolignol moiety and a carboxylate moiety, wherein the isolated labeled lignin fragments comprise two or more of:
         a first type in which the monolignol moiety is a labeled monolignol moiety and the carboxylate moiety is an un-labeled carboxylate moiety;
         a second type in which the monolignol moiety is an un-labeled monolignol moiety and the carboxylate moiety is a labeled carboxylate moiety; and
         a third type in which the monolignol moiety is a labeled monolignol moiety and the carboxylate moiety is a labeled carboxylate moiety; and
      detecting a relative amount of at least one of the first type of isolated labeled lignin fragment, the second type of isolated labeled lignin fragment, and the third type of isolated labeled lignin fragment with respect to another of the first type of isolated labeled lignin fragment, the second type of isolated labeled lignin fragment, and the third type of isolated labeled lignin fragment.

2. The method of claim 1, wherein the labeled acetic anhydride is deuterium-labeled acetic anhydride.

3. The method of claim 1, wherein step (a) comprises derivatizing the lignin with an acetyl halide.

4. The method of claim 1, wherein step (a) comprises derivatizing extracted cell wall material or isolated lignin from plants, plant parts, or plant cells.

5. The method of claim 1, wherein the carboxylate moiety is selected from the group consisting of p-hydroxybenzoate, p-coumarate, ferulate, and sinapate.

6. The method of claim 1, wherein the detecting the relative amount of at least one of the first type of isolated labeled lignin fragment, the second type of isolated labeled lignin fragment, and the third type of isolated labeled lignin fragment with respect to another of the first type of isolated labeled lignin fragment, the second type of isolated labeled lignin fragment, and the third type of isolated labeled lignin fragment comprises:
   fragmenting each of the isolated labeled lignin fragments into sub-fragments, wherein each sub-fragment comprises a first sub-fragment and a second sub-fragment, wherein each first sub-fragment comprises at least a portion of the monolignol moiety and is a labeled first sub-fragment or an un-labeled first sub-fragment, wherein each second sub-fragment comprises at least a portion of the carboxylate moiety and is a labeled second sub-fragment or an un-labeled second sub-fragment; and
   detecting a relative amount of the labeled first sub-fragments with respect to the un-labeled first sub-fragments, a relative amount of the labeled second sub-fragments with respect to the un-labeled second sub-fragments, or a relative amount of the labeled first sub-fragments with respect to the un-labeled first sub-fragments and a relative amount of the labeled second sub-fragments with respect to the un-labeled second sub-fragments.

* * * * *